United States Patent
Koh et al.

(10) Patent No.: US 8,447,389 B2
(45) Date of Patent: May 21, 2013

(54) METHODS AND SYSTEMS TO MONITOR AND IDENTIFY TRANSIENT ISCHEMIA

(75) Inventors: Steve Koh, South Pasadena, CA (US); Michael Yang, Thousand Oaks, CA (US); Ryan Rooke, Redondo Beach, CA (US); Stuart Rosenberg, Castaic, CA (US); Wenbo Hou, Lancaster, CA (US)

(73) Assignee: Pacesetter, Inc., Sylmar, CA (US)

( * ) Notice: Subject to any disclaimer, the term of this patent is extended or adjusted under 35 U.S.C. 154(b) by 326 days.

(21) Appl. No.: 12/861,573

(22) Filed: Aug. 23, 2010

(65) Prior Publication Data
US 2012/0046564 A1   Feb. 23, 2012

(51) Int. Cl.
*A61B 5/0452* (2006.01)
(52) U.S. Cl.
USPC .......................................................... 600/509
(58) Field of Classification Search
USPC ................................................. 600/508–509
See application file for complete search history.

(56) References Cited

U.S. PATENT DOCUMENTS

| | | | |
|---|---|---|---|
| 7,457,664 B2 | 11/2008 | Zhang et al. | |
| 2002/0016548 A1* | 2/2002 | Stadler et al. | 600/509 |
| 2006/0069322 A1 | 3/2006 | Zhang et al. | |
| 2006/0116593 A1 | 6/2006 | Zhang et al. | |
| 2006/0253044 A1 | 11/2006 | Zhang et al. | |
| 2006/0253162 A1 | 11/2006 | Zhang et al. | |
| 2011/0060234 A1* | 3/2011 | Zhou et al. | 600/509 |

OTHER PUBLICATIONS

Birnbaum, Yochai MD et al., "Prediction of the Level of Left Anterior Descending Coronary Artery Obstruction During Anterior Wall Acute Myocardial Infarction by the Admission Electrocardiogram," Am J Cardiol. 1993;72:823-826.
Sgarbossa, Elena B. MD et al., "Electrocardiographic diagnosis of acute myocardial infarction: Current concepts for the clinician," Am Heart J. 2001;141:507-517.
Wagner, Galen S. Md et al., "AHA/ACCF/HRS Recommendations for the Standardization and Interpretation of the Electrocardiogram," J Am Coll Cardiol. 2009;53:1003-1011.

* cited by examiner

*Primary Examiner* — Carl H Layno
*Assistant Examiner* — Paula J Stice

(57) ABSTRACT

A system and method are provided for monitoring ischemic development. The system and method identify a non-physiologic event and obtain cardiac signals along multiple sensing vectors, wherein at least a portion of the sensing vectors extend to or from electrodes located proximate to the left ventricle. The system and method monitor a segment of interest in the cardiac signals obtained along the multiple sensing vectors to identify deviations in the segment of interest from a baseline. The system and method record at least one of timing or segment shift information associated with the deviations in the segments of interest; and identify at least one of size, direction of development or rate of progression of an ischemia region based on the at least one of timing or segment shift information.

23 Claims, 16 Drawing Sheets

METHODS AND SYSTEMS TO MONITOR AND IDENTIFY TRANSIENT ISCHEMIA

FIELD OF THE INVENTION

Embodiments of the present invention pertain generally to implantable and external medical devices and more particularly pertain to methods and systems that monitor cardiac events and differentiate transient ischemia from persistent spreading ischemia.

BACKGROUND OF THE INVENTION

Medical devices are implanted in patients to monitor, among other things, electrical activity of a heart and to deliver appropriate electrical and/or drug therapy, as required. Implantable medical devices ("IMDs") include, for example, pacemakers, cardioverters, defibrillators, implantable cardioverter defibrillators ("ICD"), and the like. The electrical therapy produced by an IMD may include, for example, pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. Certain types of arrhythmias are caused by ischemia.

Cardiac ischemia is a condition whereby the heart tissue does not receive adequate amounts of oxygen. Ischemia arises during angina, coronary angioplasty, and many other conditions that compromise blood flow to a region of heart tissue. When blockage of an artery is sufficiently severe, the cardiac ischemia may progress into an acute myocardial infarction ("AMI"), which also is referred to as a myocardial infarction ("MI") or a heart attack. Cardiac ischemia and myocardial infarction are usually caused by blockage of an artery leading to the heart tissue. The heart will experience ischemia in different regions based on which artery experiences the blockage and where the blockage is along the artery. For example, anterior wall ischemia/infarction is generally due to blockage in the left anterior descending coronary artery. Occlusion of the proximal left anterior descending coronary artery above the first septal and first diagonal branches may cause ischemia/infarction in the basal portion of the left ventricle, as well as in the anterior and lateral walls and the interventricular septum.

Past studies have been conducted to interpret the results of electrocardiograph (ECG) signals that are collected by external devices that are connected to 12 leads attached to the chest and back of a patient. The ECG signals have been analyzed in an effort to diagnose ischemia and infarction. ECG changes, that are association with ischemia and infarction, include hyper acute T wave changes, ST segment elevation and/or depression, changes in QRS complex and inverted T waves. Changes in the ST segment may be produced by the flow of currents generated by voltage gradients across the boundary between ischemic and non-ischemic regions during the resting and plateau phases of the ventricular action potential which corresponds to the TQ and ST segments of the ECG signals.

When certain leads within an external ECG system detect substantial ST segment shifts, this may be an indicator of potential blockage in certain arteries. However, the conventional external ECG analysis has certain limitations. For example, the patient must be coupled to the external ECG system while the patient is experiencing ischemia. Not all types of ischemia persist permanently. When a non-physiologic event occurs, a local region or local regions of the heart, not previously in an ischemic state, may enter an ischemic state. The ischemic region progresses over a period of time following the non-physiologic event. For example, the ischemic region may grow or develop in a particular direction. After a period of time, regions that experience certain types of ischemia revert back to a normal non-ischemic state.

Conventional ECG systems may not be coupled to the patient at the time period following a non-physiologic event during which the region is ischemic. Further, when a conventional ECG system is connected to a patient while a region of the heart is in an ischemic state, the ECG system is unable to characterize the dynamic behavior of the ischemic region. For example, conventional external ECG systems are unable to identify i) changes in a size of an ischemic region, ii) a direction of the progression of the ischemic region, or iii) a rate at which the ischemic region progresses. Moreover, conventional external ECG systems are not able to provide quantitative information regarding the progression of an ischemic region from the time at which a non-physiologic event occurs until the ischemic region enters a stable persistent state or reverts to a non-ischemic state.

Many patients at risk of cardiac ischemia have pacemakers, ICDs or other medical devices implanted therein. The implanted device senses an intra-cardiac electrogram ("IEGM"). IEGMs are composed of various waves and segments that represent the heart depolarizing and repolarizing. The ST segment in an IEGM represents the portion of the cardiac signal between ventricular depolarization and ventricular repolarization. Deviation of the ST segment from a baseline is a result of injury to cardiac muscle, variations in the synchronization of ventricular muscle depolarization, drug or electrolyte influences, or the like. Techniques have been developed to identify the presence of cardiac ischemia using implanted medical devices by identifying variations in the ST segment from the baseline cardiac signal that occur during cardiac ischemia.

However, conventional implantable devices have not yet been able to differentiate between different types of ischemia. Not all ischemic events progress to the state of an AMI. Instead, some ischemic events may be characterized as transient ischemia, while other ischemic events represent persistent spreading ischemia. One difference between transient ischemia and spreading ischemia is that transient ischemia generally reverses, while spreading ischemia often leads to permanent cardiac tissue damage and an AMI. Therefore, a transient ischemic event may occur for a relatively short period of time (e.g., a few hours) and go undetected by an external ECG system, but may not persist, nor develop into an AMI.

It has been suggested that, when less than 5% of the myocardium tissue is in an ischemic state, this condition may not be clinically significant. However, when more than 10% of the myocardial tissue exhibits a transient ischemic state, then it may be appropriate for the clinician to intervene for treatment such as utilizing an angiogram, balloon catheter, stents or medication. Often transient ischemia goes away by itself without intervention.

A need remains for improved methods and systems to monitor ischemic events and differentiate transient ischemia from persistent spreading ischemia.

SUMMARY

In accordance with one embodiment a method is provided to provide a 2D graphic about ischemic progression using an implanted device and a programmer (or any handheld unit). In accordance with one embodiment a method is provided to differentiate transient ischemia and myocardial infarction based on time information, location of an ischemic region, area of an ischemic region and rate of progression in changes or movement in an ischemic region.

In accordance with one embodiment a method is provided for monitoring ischemic development. The method includes identifying a non-physiologic event; obtaining cardiac signals along multiple sensing vectors, wherein at least a portion of the sensing vectors extend to or from electrodes located proximate to the left ventricle; and monitoring a segment of interest in the cardiac signals obtained along the multiple sensing vectors to identify deviations in the segment of interest from a baseline. The method also includes recording at least one of timing or segment shift information associated with the deviations in the segments of interest; and identifying at least one of size, direction of development or rate of progression of an ischemia region based on the at least one of timing or segment shift information.

Optionally, the identifying operation may identify the rate of progression and provides graphical information regarding ischemic progression. The identifying operation may include differentiating transient ischemia from persistent spreading ischemia. The method may include providing a first electrode proximate at least one of a right ventricle, right atrium and superior vena cava; providing multiple LV electrodes proximate to the left ventricle, wherein the sensing vectors extend between the first electrode and the multiple LV electrodes. The monitoring operation monitors the segment of interest as collected along multiple sensing vectors that extend through different portions of the LV. The deviations may represent shifts in ST segments away from a baseline ST segment level. The recording operation may include populating a vector table with time and shift information associated with the deviations by the segment of interest.

Optionally, the method may further comprise calculating 2 dimension (2D) gradients in connection with the sensing vectors, the 2D gradient representing a change in the segment shift information per unit of time. The identifying operation identifies the size of the ischemia at successive points in time. The method may further comprise classifying an event as transient ischemia when the size of the ischemic region decreases over time. The method may further comprise classifying an event as myocardial infarction when the ischemic region spreads by a predetermined amount and persists for a predetermined period of time.

In accordance with one embodiment a system is provided for monitoring ischemic development. The system includes at least one lead having electrodes to obtain cardiac signals along multiple sensing vectors, wherein at least a portion of the sensing vectors extend to or from electrodes located proximate to the left ventricle. An implantable device identifies a non-physiologic event and a monitor module monitors a segment of interest in the cardiac signals obtained along the multiple sensing vectors and that occurred after the non-physiologic event. The ischemia monitor module identifies deviations in the segment of interest from a baseline. Memory records at least one of timing or segment shift information associated with the deviations in the segments of interest and an analysis module identifies at least one of size, direction of development or rate of progression for an ischemia region based on the at least one of timing or segment shift information.

Optionally, a first lead has a first electrode proximate to at least one of a right ventricle, right atrium and superior vena cava and a second lead has multiple LV electrodes proximate to the left ventricle, wherein the sensing vectors extend between the first electrode and the multiple LV electrodes.

DETAILED DESCRIPTION

Figure 1A:
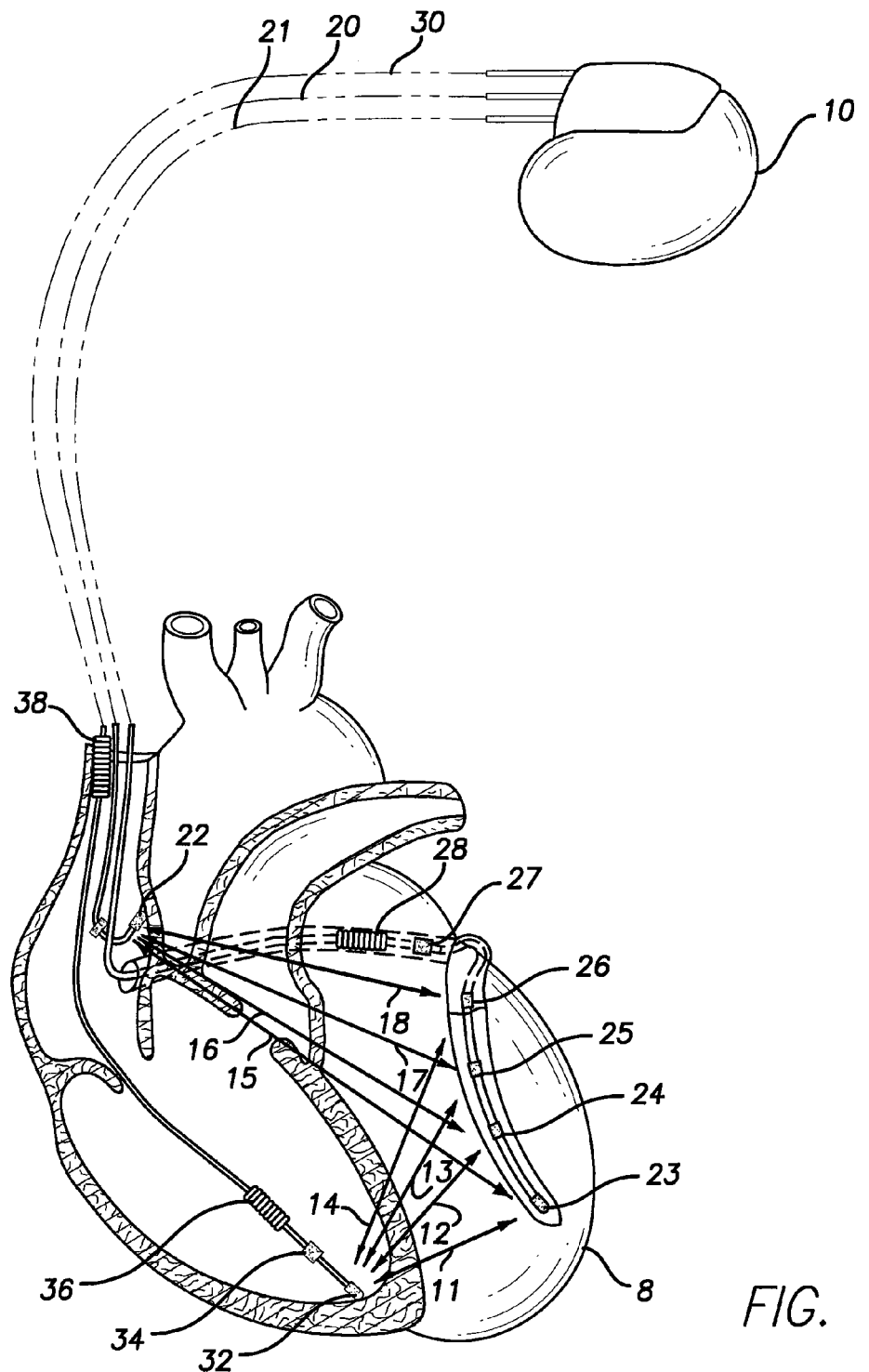
FIG. 1A illustrates a diagram of an implantable medical device with multiple LV electrodes that forms sensing vectors in accordance with an embodiment.
Figure 1B:
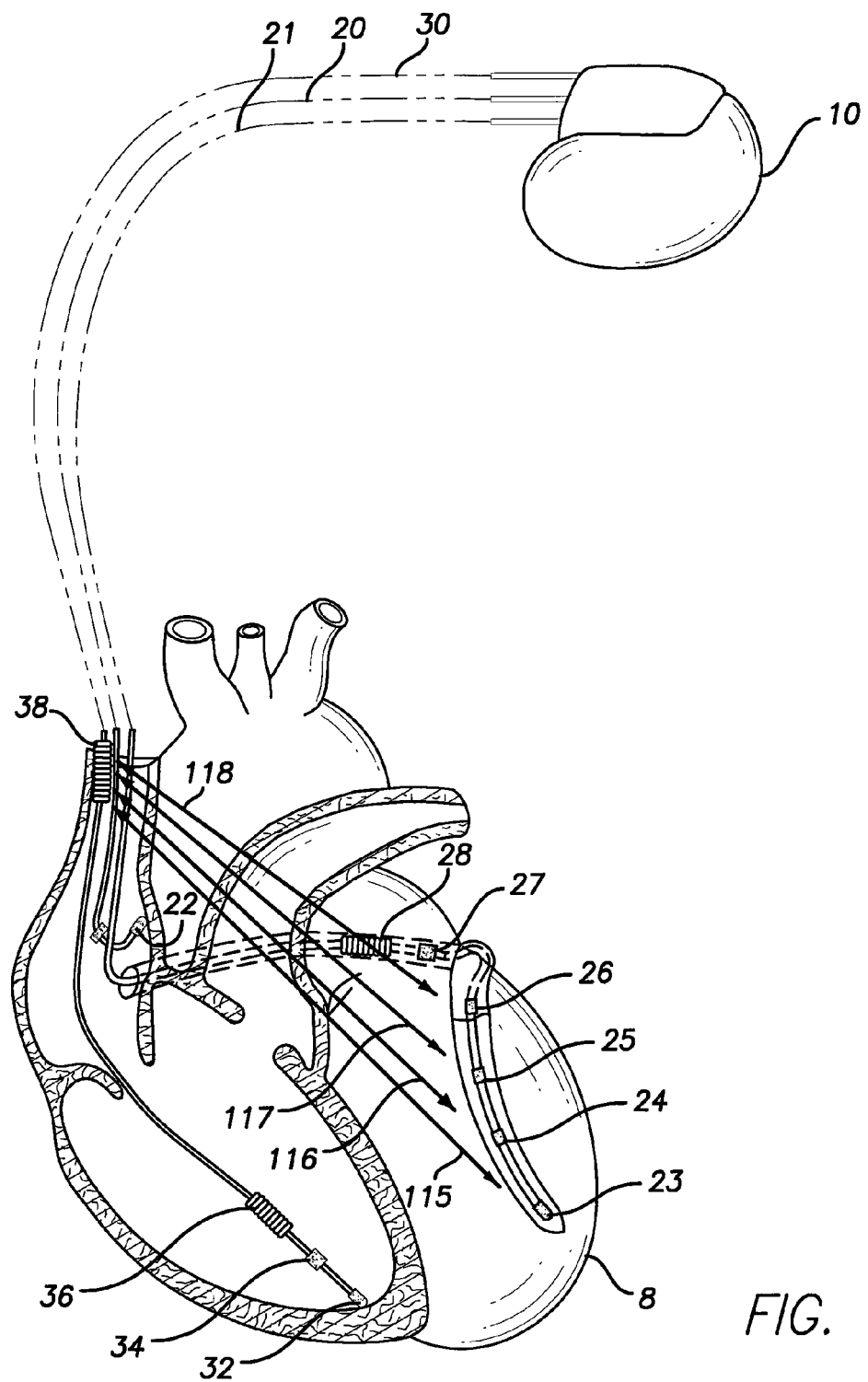
FIG. 1B illustrates a diagram of an implantable medical device with multiple LV electrodes that form sensing vectors in accordance with an embodiment.

FIGS. 1A and 1B illustrate diagrams of an implantable medical device (IMD) 10 in electrical communication with leads 20, 21 and 30 implanted in or proximate a patient's heart 8 for delivering single or multi-chamber stimulation (e.g.

pacing, ATP therapy, high voltage shocks and the like). As explained below, the leads 20, 21 and 30 are used to sense various events (e.g., ischemia, VT and VF) and to deliver, among other things, pacing, defibrillation and antitachycardia pacing (ATP) therapies. The device 10 is programmable, by an operator, to set certain operating parameters, as well as therapy-related parameters. The device 10 is configured to operate with various configurations of leads. Exemplary lead configurations are shown in the figures. The device 10 is configured to deliver various types of therapies. The IMD 10 may be a pacing device, a pacing apparatus, a cardiac rhythm management device, an implantable cardiac stimulation device, an implantable cardioverter/defibrillator (ICD) and/or a cardiac resynchronization therapy (CRT) device.

The right atrial lead 20 has, by way of example, a right atrial (RA) tip electrode 22, which typically is implanted in the patient's right atrial appendage. The right ventricular lead 30 includes an RV tip electrode 32, an RV ring electrode 34, an RV coil electrode 36, and a superior vena cava (SVC) coil electrode 38 (also known as a right atrial (RA) coil electrode). The right ventricular lead 30 is capable of sensing cardiac signals, and delivering stimulation in the form of pacing and shock therapy to the SVC and/or right ventricle.

The left ventricular (LV) lead 21 may be inserted into a left anterior coronary artery or a left posterior coronary artery proximate to the left ventricle. Optionally, the LV lead 21 may be inserted into the LV chamber or inserted along another vein or artery extending along the heart wall proximate to the left ventricle. Optionally, the LV lead 21 may be formed as a patch or mesh net that is secured to or located adjacent to an exterior wall of the left ventricle. The LV lead 21 receives atrial and ventricular cardiac signals and delivers left ventricular pacing therapy using a left ventricular (LV) electrode 23, and intermediate LV electrodes 24, 25 and 26. Left atrial pacing therapy may be delivered using, for example, first and/or second left atrial (LA) electrodes 27 and 28. Some or all of the LV and LA electrodes 23-29 may represent sensing sites, where cardiac signals are sensed, and/or may represent therapy sites.

In the examples of FIGS. 1A and 1B, the LV electrodes 23-26 are spaced apart generally evenly from one another along the lateral wall of the left ventricle. The LV lead 21 may include more or fewer LA electrodes 27 and 28 proximate to the left atrium. Optionally, more or fewer LV electrodes may be utilized. Optionally, the LV electrodes may be separated more or positioned closer to one another. Optionally, all or a portion of the LV electrodes may be shifted along the LV lead 21 until positioned proximate to the mitral valve, aortic valve, or the left atrial ports to/from the pulmonary veins.

Embodiments are described herein, whereby one or more non-LV electrodes and multiple LV electrodes are utilized to define sensing vectors that extend through different regions of the heart. The use of multiple LV sensing sites affords improved characterization and understanding of dynamic progression of ischemic events and of which regions experience transitory or persistent ischemic states. Information collected along these sensing vectors is utilized to produce ischemia progression data that is stored in the IMD 10. The progression data is later transmitted from the IMD 10 and used to analyze dynamic ischemic progression, such as (1) a size of developing ischemia/infarction, (2) a direction of ischemia development, and (3) a rate of ischemia development. The ischemia progression data may be downloaded via (1) a programmer during a clinic follow-up visit, (2) a patient care network such as the Merlin.net® network or (3) a programmer in an emergency room (e.g., when a patient checks in after experiencing chest pain). As another example, the ischemia progression data may be used to prompt the patient to go to the emergency room.

FIGS. 1A and 1B illustrate an electrode configuration with non-LV electrodes and LV electrodes defining sensing vectors that extend through desired regions of the heart 8. For simplicity, the sensing vectors are split between FIGS. 1A and 1B, but the sensing vectors of FIGS. 1A and 1B are utilized simultaneously. For example, a first non-LV electrode may be located proximate to at least one of the right ventricle, the right atrium and/or the superior vena cava. One or a set of second electrodes, which represent LV electrodes, are located proximate to the left ventricle. By way of example only, FIG. 1A illustrates first and second subsets of sensing vectors. The first subset of sensing vectors 11-14 is formed between RV tip electrode 32 and the LV electrodes 23-26. The second subset of sensing vectors 15-18 is formed between RA tip electrode 22 and the LV electrodes 23-26. FIG. 1B illustrates a third subset of sensing vectors 115-118 that are formed between the SVC electrode 38 and the LV electrodes 23-26. The subsets of sensing vectors 11-18 and 115-118 afford the ability to obtain cardiac signals from the near field proximate to the LV electrodes 23-26 for designated regions of interest within the heart (e.g., the anterior wall). As explained hereafter, segments of interest are analyzed from these cardiac signals.

Figure 1C:
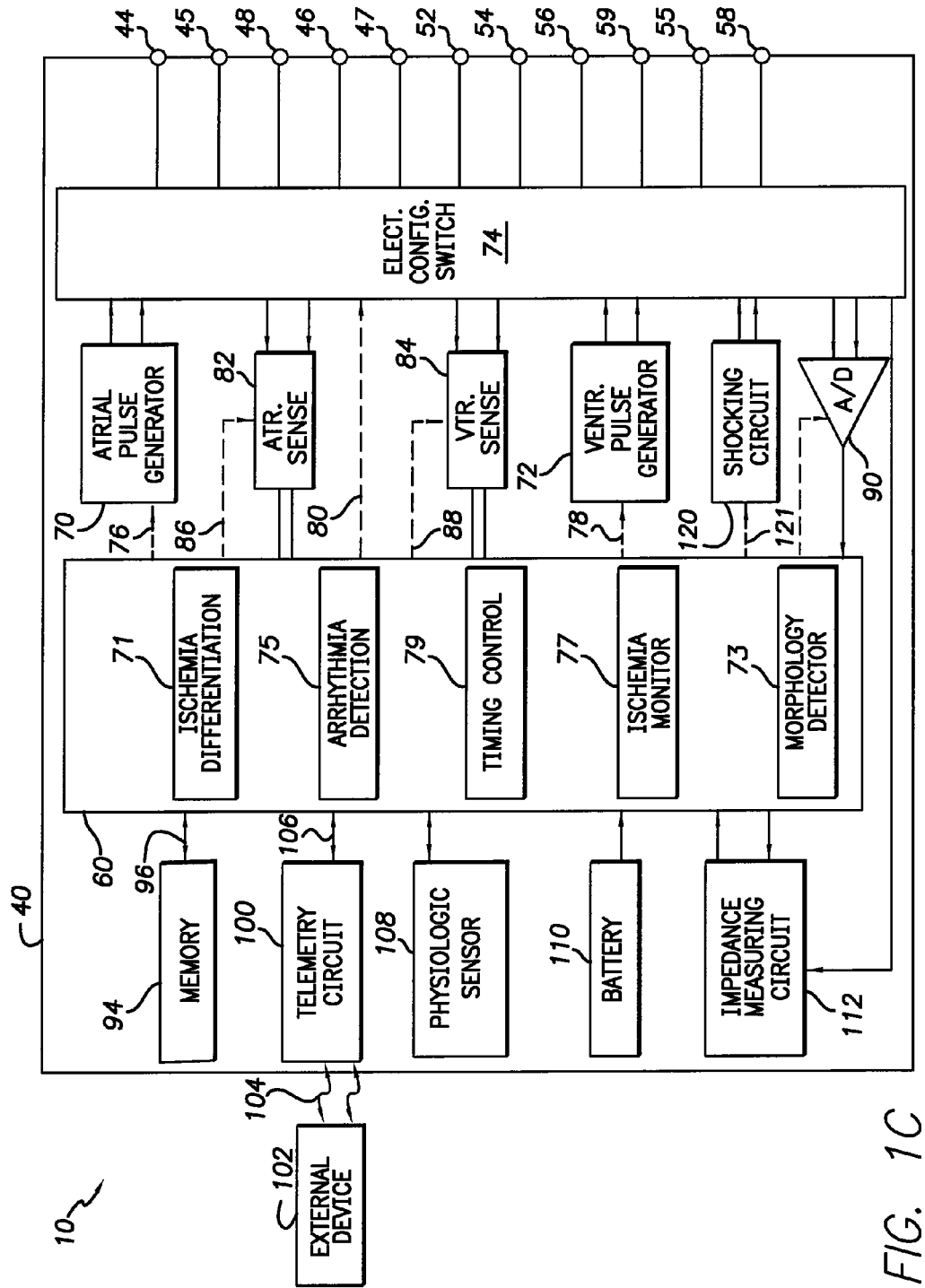
FIG. 1C illustrates a block diagram of an implantable device implemented in accordance with an embodiment of the present invention.

FIG. 1C illustrates a block diagram of the IMD 10, which is capable of treating both fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of treating the appropriate chamber(s) with cardioversion, defibrillation and pacing stimulation.

The housing 40 for the IMD 10, shown schematically in FIG. 1C, is often referred to as the "can", "case" or "case electrode" and may be programmably selected to act as the return electrode for some or all "unipolar" modes. The housing 40 may further be used as a return electrode alone or in combination with one or more of the coil electrodes, 29, 36 and 38 of FIG. 1, for shocking purposes. The housing 40 further includes a connector (not shown) having a plurality of terminals, 44, 45, 46, 47, 48, 52, 54, 55, 56, 58, and 59. To achieve sensing, pacing and shocking in desired chambers of the heart, the terminals 44-59 are connected to corresponding combinations of electrodes 22-36.

An electrode configuration switch 74 connects the sensing electronics to the desired ones of the terminals 44-59 of corresponding sensing electrodes. For example, terminals 55-59 may be coupled to LV electrodes 23-26. The switch 74 may connect terminals 55-59 to one or more ventricular sensing circuits 84, which provides signals, representative of cardiac activity, to the microcontroller 60. The circuit 84 may amplify, filter, digitize and/or otherwise process the sensed signals from the LV electrodes 23-26. The circuit 84 may provide separate, combined or difference signals to the microcontroller 60 representative of the sensed signals form the LV electrodes 23-26. The circuit 84 may also receive sensed signals from RV electrodes. The atrial sensing circuit 82 is connected through the switch 74 to desired RA and/or LA electrodes to sense RA and/or LA cardiac activity.

The IMD 10 includes a programmable microcontroller 60 that controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. The microcontroller 60 includes the ability to process or monitor input signals (data) as controlled by a program code stored in memory. The details of the design and operation of the microcontroller 60 are not critical to the present invention. Rather, any suitable microcontroller 60 may be used.

The microcontroller 60 includes an arrhythmia detection module 75 that analyzes sensed signals and determines when a non-physiologic event, namely an abnormal sinus rhythm. For example, a non-physiologic event may be an arrhythmia. The detection module 75 receives signals sensed by electrodes located at one or more of the sensing sites. For example, the detection module 75 may analyze cardiac signals from an RA electrode, RV electrode and/or multiple LV electrodes. The detection module 75 detects the non-physiologic event, such as an arrhythmia that represents a tachycardia or fibrillation.

The microcontroller 60 includes a morphology detection module 73 that may perform wave morphology analysis to characterize segments of interest within cardiac signals (e.g., the PQ segment, QRS complex, ST segment or T wave peak). The microcontroller 60 includes an ischemia monitoring module 77. The module obtains cardiac signals along multiple sensing vectors, wherein at least a portion of the sensing vectors extend to or from electrodes located proximate to the left ventricle. The module 77 monitors a segment of interest in the cardiac signals to identify deviations of the segment of interest. The segment of interest may represent the ST segment, the PQ segment, the QRS complex, the T wave peak and the like. The segment of interest may be obtained from a cardiac signal collected from one cardiac cycle, or from a cardiac signal formed from an average over a series of cardiac cycles. The deviation may be measured with respect to a baseline segment threshold, such as a baseline ST segment level. The baseline segment threshold may be stored in memory 94 at the time of manufacture, programmed at the time of implant, programmed after implant, or updated remotely over the patient care network. Optionally, the baseline segment threshold may be acquired by the IMD 10 when the microcontroller 60 determines that the heart is exhibiting a normal sinus rhythm. Optionally, the module 77 may identify, as the deviations in the segment of interest, changes in the PQ segment, changes in the ST morphology changes in the QRS complex, changes in the T-wave peak and/or changes in the T-wave slope.

Based on the deviations identified, the module 77 records ischemia progression data in memory in the IMD 10. The progression data may include at least one of timing information or segment shift information associated with the deviations in the segments of interest. As explained hereafter, during the recording operation, the module 77 creates and populates a vector table with timing information and/or segment shift information associated with the deviations detected in the segment of interest. The vector table may be stored temporarily on the microcontroller 60 and then saved to memory 94 periodically as the vector table is created or updated. Optionally, the vector table may be written to the memory 94 once completed.

The microcontroller 60 may also include an ischemia differentiation module 71 that analyzes the progression data stored in the vector tables. As explained hereafter, the module 71 may identify at least one of size, direction of ischemic development or rate of progression of an ischemia development. For example, the module 71 may identify the rate of progression. The module 71 may identify the size, direction and rate by calculating gradient information, such as 2 dimension (2D) gradients, in connection with the data in the vector tables. Each 2D gradient is associated with a cell or location in the vector table. Each 2D gradient has a direction and magnitude, where the direction points toward the greatest rate of increase between the cells in the vector table and the magnitude corresponds to the greatest rate of change. The 2D gradients are saved in memory 94 and then transmitted from the IMD 10. The 2D gradients indicate the changes in the timing of the segment shifts. The module 71 may identify the size of the ischemia at successive points in time. The module 71 may classify an event as transient ischemia when the size of the ischemic region decreases over time. The module 71 may classify an event as myocardial infarction when the ischemic region spreads and persists over time. The module 71 may then transmit directions to a home based external device, through a patient care network, to inform the patient when some action is warranted.

As shown in FIG. 1C, an atrial pulse generator 70 and a ventricular pulse generator 72 generate pacing and ATP stimulation pulses for delivery by desired electrodes. The electrode configuration switch 74 (also referred to as switch bank 74) controls which terminals 44-59 receive one or more pulses of a therapy from pulse generators 70 and 72. The atrial and ventricular pulse generators, 70 and 72, may include dedicated, independent pulse generators, multiplexed pulse generators, shared pulse generators or a single common pulse generator. The pulse generators 70 and 72 are controlled by the microcontroller 60 via appropriate control signals 76 and 78, respectively, to trigger or inhibit stimulation pulses. The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, and the like.

The switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, co-bipolar, etc.) by selectively closing the appropriate combination of switches (not specifically shown). Atrial sensing circuits 82 and ventricular sensing circuits 84 may also be selectively coupled to the RA lead 20, LV lead 21, and the RV lead 30, through the switch 74 for detecting the presence of cardiac activity in each of the four chambers of the heart. The switch 74 determines the "sensing polarity" of the cardiac signal by selectively closing the appropriate switches. The outputs of the atrial and ventricular sensing circuits 82 and 84 are connected to the microcontroller 60. The sensing circuits 82 and 84, in turn, receive control signals over signal lines 86 and 88 from the microcontroller 60 to control the gain, threshold, the polarization charge removal circuitry (not shown), and the timing of any blocking circuitry (not shown) coupled to the inputs of the sensing circuits 82 and 86.

For arrhythmia detection, the device 10 utilizes the atrial and ventricular sensing circuits 82 and 84 to sense cardiac signals, such as groups of cardiac signals from the sensing vectors 11-18 and 115-118 for individual cardiac cycles. The arrhythmia detection module 75 determines whether a rhythm is physiologic or pathologic. As used herein "sensing" is the receipt or noting of an electrical signal, and "detection" is the processing of these sensed signals and determining the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and/or various other characteristics (e.g., sudden onset, stability, physiologic sensors, morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 samples cardiac signals across any pair of desired electrodes. The data acquisition system 90 may be coupled to the microcontroller 60, or other detection circuitry, for detecting an evoked response from the heart 8 in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 60 is further coupled to a memory 94 by a suitable data/address bus 96, wherein the programmable operating and therapy-related parameters used by the microcontroller 60 are stored and modified, as required, in order to customize the operation of the IMD 10 to suit the needs of a particular patient. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart 8 within each respective tier of therapy.

The operating and therapy-related parameters may be non-invasively programmed into the memory 94 through a telemetry circuit 100 in telemetric communication with the external device 102, such as a programmer, trans-telephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104. The telemetry circuit 100 transmits to the external device 102, among other things, the vector tables and ischemia progression data. The telemetry circuit 100 may also transmit to the external device 102, ischemia analysis information, such as the gradients, ischemia region size, direction of development, rate of progression and the like.

The IMD 10 may include a physiologic sensor 108 to adjust pacing stimulation rate according to the exercise state of the patient. The physiological sensor 108 may further be used to detect changes in cardiac output, changes in the physiological condition of the heart, or diurnal changes in activity (e.g., detecting sleep and wake states). The microcontroller 60 responds by adjusting the various pacing parameters (such as rate, AV Delay, V-V Delay, etc.) at which the atrial and ventricular pulse generators, 70 and 72, generate stimulation pulses.

The battery 110 provides operating power to all of the circuits shown in FIG. 1C. An impedance measuring circuit 112 monitors lead impedance during the acute and chronic phases for proper lead positioning or dislodgement; detects operable electrodes and automatically switches to an operable pair if dislodgement occurs; measures respiration or minute ventilation; measures thoracic impedance for determining shock thresholds; detects when the device has been implanted; measures stroke volume; and detects the opening of heart valves, etc.

The microcontroller 60 further controls a shocking circuit 120 by way of a control signal 121. The shocking circuit 120 generates stimulating pulses of low (up to 0.5 joules), moderate (0.5-10 joules), or high energy (11 to 40 joules), as controlled by the microcontroller 60. Stimulating pulses are applied to the patient's heart 8 through at least two shocking electrodes, and as shown in this embodiment, selected from the left atrial (LA) coil electrode 29, the RV coil electrode 36 the SVC coil electrode 38 and/or the housing 40.

Figure 2:
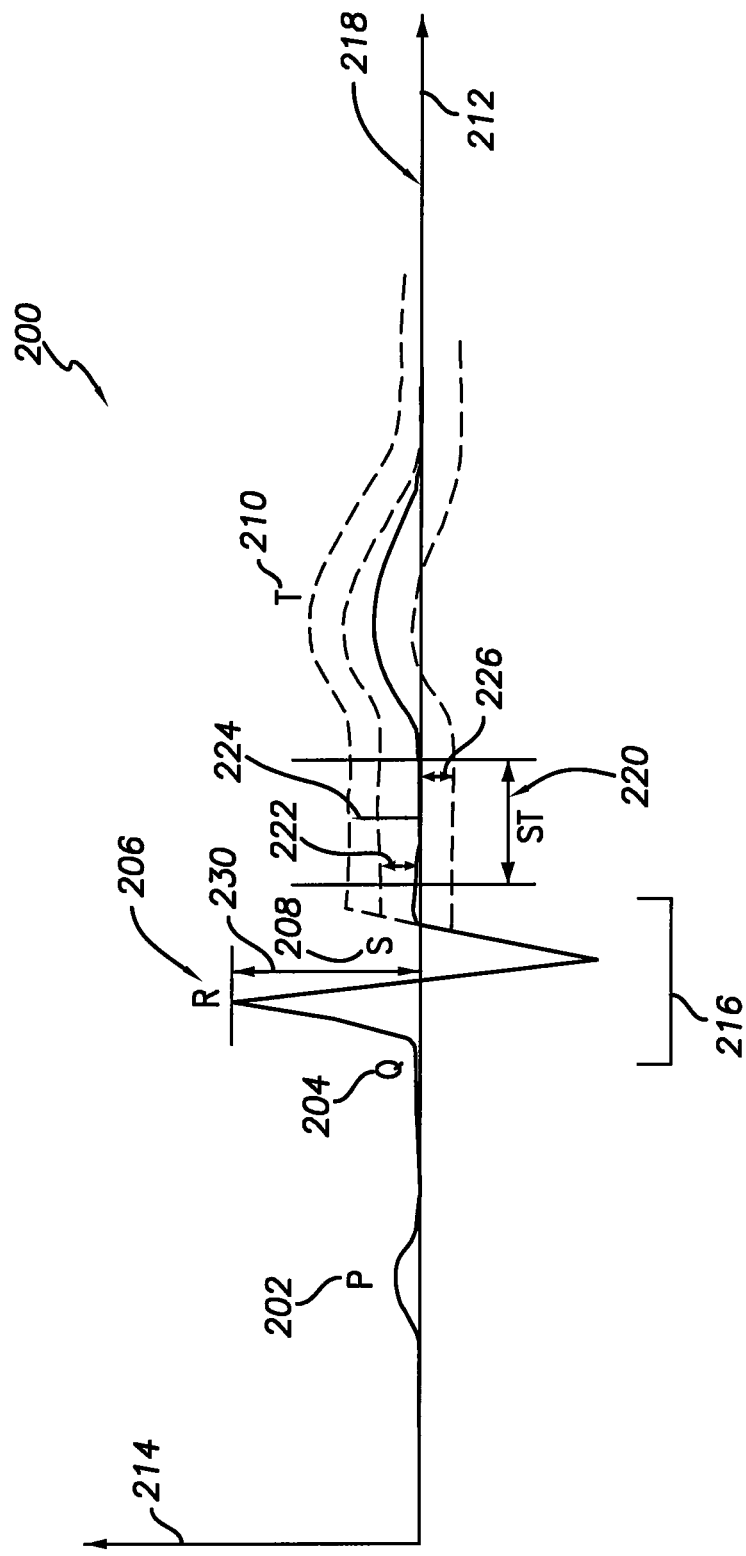
FIG. 2 illustrates an exemplary cardiac signal that may be collected along one sensing vector

FIG. 2 illustrates an exemplary cardiac signal that may be collected along a sensing vector. The signal in FIG. 2 is shown only as an illustration. While the shape of signals sensed along the sensing vectors 11-18 and 115-118 will vary, each signal will have each of the segments in FIG. 2. The cardiac signal corresponds to a single cardiac cycle 200 that includes a P-wave 202, a Q-wave 204, an R-wave 206, an S-wave 208, and a T-wave 210. The horizontal axis 212 represents time, while the vertical axis 214 is defined in units of voltage. A QRS complex 216 is composed of the Q-wave 204, the R-wave 206, and the S-wave 208. The portion of the signal between the S-wave 208 and T-wave 210 constitutes an ST segment 220.

In a normal sinus event, the R-wave 206 and the ST segment 220 remain approximately the same for a plurality of cardiac cycles and/or a plurality of sets of cardiac cycles. For example, the amplitude 230 of the R-wave 206 may be approximately the same for each R-wave 206 in a plurality of cardiac cycles in a set, and approximately the same for the cardiac cycles in a plurality of sets of cardiac cycles. In another example, the ST segment 220 may be located at approximately the same location with respect to a baseline 218 for each cardiac cycle in a set of cardiac cycles, and approximately the same for the cardiac cycles in a plurality of sets of cardiac cycles.

However, when a cardiac signal is sensed along a sensing vector that traverses an ischemic region of the heart, the R-wave 206 and/or the ST segment 220 may deviate from a normal shape or level. The amplitude 230 of the R-wave 206 may increase or decrease between cardiac cycles or sets of cardiac cycles. For example, the ST segment 220 may experience an upward shift 222, 224 or a downward shift 226 with respect to a baseline 218. The ST segment shifts 222-226 may occur when a region is in an ischemic state. For example, the ST segment shifts 222-226 may arise because of differences in the electrical potential between cells that have become ischemic and those that are still receiving normal blood flow. The ST segment shift 222-226 is identified by the ischemia monitor module 77 by comparing a current ST segment level with a baseline ST segment threshold. When the current ST segment exceeds the baseline ST segment threshold, this is an indication that the associated region has entered an ischemic state.

Figure 3:
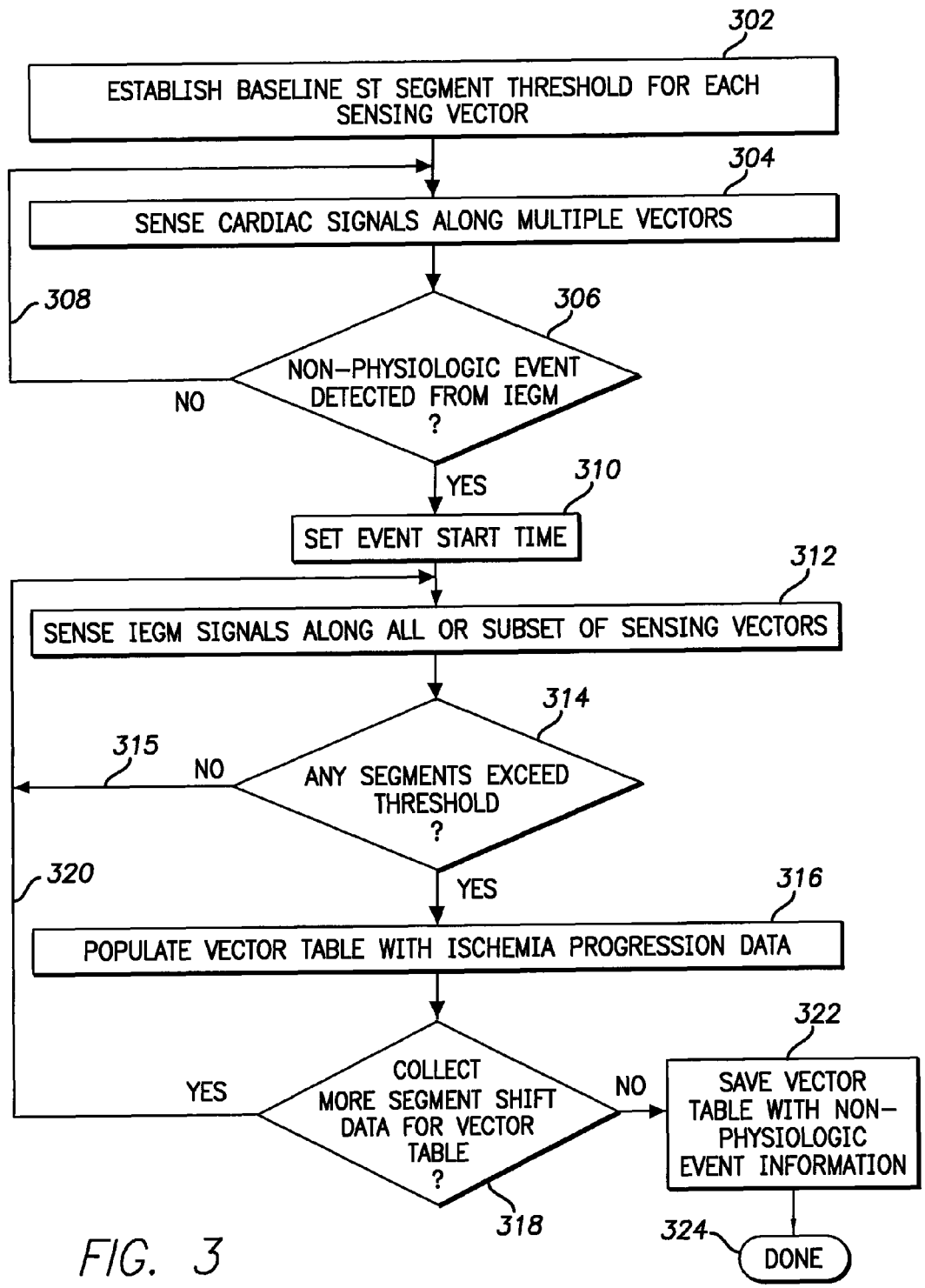
FIG. 3 illustrates a processing sequence performed in accordance with an embodiment for monitoring a segment of interest in multiple cardiac signals and collecting ischemia progression data during ischemic development.

FIG. 3 illustrates a processing sequence carryout in accordance with an embodiment for monitoring ischemic development and recording progression data associated with different regions of the heart. Beginning at 302, a baseline segment threshold(s) is established for a segment of interest (such as the ST segment) in accordance with multiple sensing vectors. The baseline segment threshold may be common or different for the sensing vectors. For example, a baseline ST segment threshold may be obtained for each of the sensing vectors 11-18 (FIG. 1A) and/or sensing vectors 115-118 (FIG. 1B).

The baseline segment threshold may be stored at the time of manufacture or programmed by a physician at the time of implant. Optionally, the baseline segment threshold may be determined periodically throughout operation through automated or periodic monitoring and analysis by the IMD 10. For example, a baseline segment threshold setting operation may be performed periodically when the IMD 10 determines that the heart is operating in a normal sinus rhythm state and thus the segment of interest (e.g., the ST segment) is expected to exhibit levels associated with healthy heart behavior.

At 304, the process begins sensing and collecting intracardiac electrogram (IEGM) signals along multiple sensing vectors. The sensing vectors may include all or a subset of the sensing vectors discussed and illustrated in the various embodiments described herein, as well as other sensing vectors not expressly discussed herein. During a single cardiac cycle, a cardiac signal is obtained along, and maintained in a one to one relation with, a corresponding one of the sensing vectors such that multiple simultaneous cardiac signals are obtained for unique corresponding paths through a region of the heart. The combinations and subsets of electrodes that are used to collect cardiac signals may be varied. At least a portion of the sensing vectors used at 304 extend to or from LV electrodes 23-26 that are located proximate to the left ventricle. The IEGM cardiac signals, that are collected along sensing vectors 11-18, include physiologic information representative of the state of the regions of the heart that are impacted by certain types of artery blockage. The IEGM cardiac signals, that are collected along sensing vectors 115-118 (FIG. 1B), include physiologic information representative of the state of the regions of the heart that are impacted by certain types of artery blockage.

For example, the LV electrodes 23-26 will collect cardiac signals that will exhibit abnormal deviations when blockage exists in certain regions. For example, one or more of the LV electrodes 23-26 will sense abnormal cardiac signals when the anterior wall is in an ischemic state or experiences an infarction, which may be due to blockage in the left anterior descending coronary artery. One or more of the LV electrodes 23-26 will sense abnormal cardiac signals when the basal portion of the left ventricle is in an ischemic state or experiences an infarction which may be due to occlusion of the proximal left anterior descending coronary artery above the first septal and first diagonal branches. One or more of the LV electrodes 23-26 will sense abnormal cardiac signals when the anterior wall, the lateral wall and/or the interventricular septum is in an ischemic state or experiences an infarction.

At 306, the process determines whether a non-physiologic event (e.g., an arrhythmia) is detected. The operation at 306 may be performed in accordance with conventional sensing electrodes located in the CAN, SVC, RV or RA. The algorithms utilized to identify the non-physiologic event may vary. Optionally, the determination at 306 may be performed based on cardiac signals obtained along sensing vectors that extend to one or more LV electrodes 23-26. When a normal sinus rhythm is detected at 306, the operation returns along 308 where new IEGM cardiac signals are collected. When at 306, a non-physiologic event is detected, flow moves to 310.

At 310, an event start time is initiated to be used as a timer in connection with subsequent analysis of segments of interest from later sensed cardiac signals.

At 312, the process collects IEGM cardiac signals along all or a subset of the sensing vectors. The collection process may be for a single cardiac cycle or for a series of cardiac cycles. For example, separate cardiac signals may be collected, during a single cardiac cycle, for all or a subset of sensing vectors 11-18 and/or 115-118. Alternatively, separate cardiac signals may be collected for all or a subset of sensing vectors 11-18 and/or 115-118, where separate cardiac signals are collected for three or more successive cardiac cycles. When a series of cardiac signals are collected for successive cardiac cycles at one time, the cardiac signals may then be combined such as through averaging. For example, a series (e.g. three) of cardiac signals may be collected along sensing vector 11 and averaged with one another. Similarly, separate series of cardiac signals may be collected along each of sensing vectors 12-18 and/or 115-118.

At 314, a segment of interest is identified from each of the acquired cardiac signals (or from each of the averages for successive cardiac signals) and analyzed. The segment of interest may be the ST segment, the QRS complex, the PQ segment, the T wave peak and the like. The segment of interest is compared to the baseline segment threshold to determine whether criteria of interest are satisfied. For example, the analysis may include a determination of whether ST segments in one or more of the IEGM cardiac signals have shifted above or below the baseline ST segment threshold. For example, the amount of segment shift in each of the current cardiac signals may be between −1.8 mV and 1.6 mV, where the baseline segment threshold is 2 mV. In this example, each of the acquired cardiac signals is deemed to be associated with regions that are not experiencing ischemia. Thus, flow returns along 315 to 312. Alternatively, one or more of the cardiac signals may have a segment of interest that has shifted by an amount that exceeds the baseline segment threshold. For example, cardiac signals along sensing vectors 14, 17 and 117 may exhibit segment shifts of 2.5 mV, 3 mV and 5 mV, respectively, which exceed the baseline segment threshold of 2 mV. The remaining cardiac signals (for sensing vectors 11-13, 15-16, 18, 115-116 and 118) may have segment shifts between −2 mV and 2 mV which do not exceed the baseline segment threshold set at 2 mV. Thus, the cardiac signals with segment shifts of −2.5 mV, 3 mV and 5 mV are deemed to be associated with regions that have entered an ischemic state, and therefore flow moves to 316.

At 316, ischemia progression data is stored. For example, the ischemia progression data may be stored in a vector table that includes multiple cells, where each cell is associated uniquely with a sensing vector. At 316, the process may update only the cells that are associated with the sensing vectors that collect cardiac signals having segment shifts that exceed the baseline segment threshold. In the above example, the cells of the vector table associated with the sensing vectors 14, 17 and 117 (having segment shifts of 2.5 mV, 3 mV and 5 mV) would be updated with current ischemia progression data. The operation at 316 tracks changes in the state of tissue regions between a normal (non-ischemic) state and an ischemic state. Thus, ischemia progression data is recorded for a particular sensing vector when a change is detected from an acceptable segment shift to a segment shift to an excessive segment shift.

The ischemia progression data may represent timing information, segment shift information, segment peak, segment slope, segment area and the like. The timing information may correspond to a delta time differential ΔT from the event start time (set in 310) up to the current time at which the abnormal segment shift was first detected for a particular sensing vector. Alternatively, the timing information may correspond to an absolute time (e.g., day, hour, minute, second) at which a first abnormal segment shift was detected along an associated sensing vector. Optionally, the ischemia progression data may include the ST segment shift information, such as a peak value of the ST segment, a length of the ST segment, a rising slope of the ST segment, a falling slope of the ST segment, an area under the ST segment and the like. Alternatively, the ST segment shift information, when saved, may correspond to the difference between the current ST segment shift measured at 314 and the baseline segment threshold established at 302. Optionally, the timing and ST segment shift information may include an average for multiple cardiac signals, a mean, a running average, a standard deviation and the like between successive ST segment shifts that are measured at 314 and/or between the baseline segment threshold and multiple ST segment shifts measured at 314.

Figure 5:
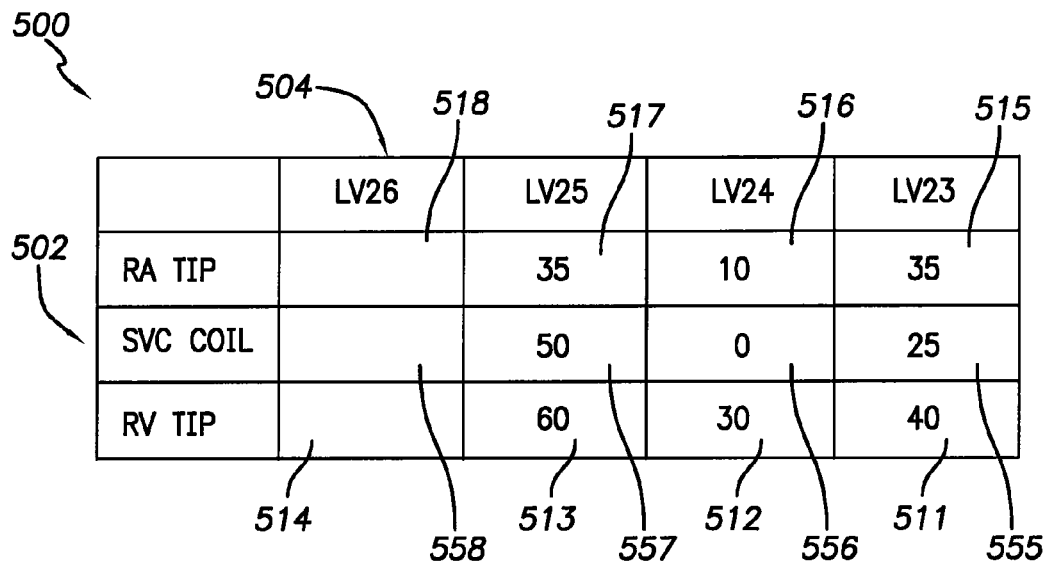
FIG. 5 illustrates an example of a vector table that may be created in connection with the process of FIG. 3.

FIG. 5 illustrates an example of a vector table that has been populated over a series of cardiac cycles in connection with the monitoring process of FIG. 3. The vector table 500 includes rows 502 that correspond to non-LV electrodes such as the RA tip, SVC coil, and RV tip. The columns 504 of the vector table 500 correspond to the LV electrodes 23-26 (denoted LV23-LV26). The columns and rows define individual cells. Cells 511-514 correspond to the sensing vectors 11-14 between the RV tip electrode 32 and the LV electrodes 23-26. Cells 515-518 correspond to the sensing vectors 15-18 between the RA tip electrode 22 and the LV electrodes 23-26. Cells 555-558 correspond to the sensing vectors 115-118 between the SCV coil electrode 38 and the LV electrodes 23-26. The cells 511-518 and 555-558 are populated with ischemia progression data (at 316 in FIG. 3) when predetermined criteria are satisfied by the cardiac signal sensed along the associated sensing vector. The criteria may be that the measured ST segment shifts upward or downward above or below the baseline ST segment threshold.

Returning to FIG. 3, during a single cardiac cycle, only one or a subset of the sensing vectors may traverse ischemic regions. Thus, during one iteration through process steps 312-316 associated with a single cardiac cycle, ischemia progression data is added to one or the corresponding subset of cells. The remaining cells do not receive any ischemia progression data during the first iteration through 312-316. Instead, the other cells receive ischemia progression data during successive cardiac cycles as the ischemic state progresses to new regions of the heart where these new regions are associated with the other sensing vectors.

FIG. 5 illustrates examples of progression data that may be saved in the vector table 500 as collected over at least an hour period following detection of a non-physiologic event. The values in the vector table 500 represent the number of minutes after the event start time (310 in FIG. 3) that an excessive segment shift occurred for a corresponding sensing vector.

The sensing vector 116 (SVC coil 38 to LV electrode 24) detected the elevated segment shift immediately at the event start time, and thus a 0 msec. value is saved in cell 556. The sensing vector 16 (RA tip 22 to LV electrode 24) detected the elevated segment shift 10 msec. after the event start time, and thus a 10 msec. value is saved in cell 516. The sensing vectors 15 and 17 (RA tip 22 to LV electrode 25 and RA tip 22 to LV electrode 23) detected the elevated segment shift 35 msec. after the event start time, and thus a 35 msec. value is saved in cells 515 and 517. The sensing vectors 117 and 115 (SVC coil 38 to LV electrodes 25 and 23) detected the elevated segment shift 50 msec. and 25 msec., respectively, after the event start time, and thus a 50 msec. value and 25 msec. value are saved in cells 557 and 555. The sensing vectors 13, 12, and 11 (RV tip 32 to LV electrodes 25, 24 and 23) detected the elevated segment shifts 60 msec., 30 msec. and 40 msec., respectively, after the event start time, and thus a 60, 30 and 40 msec. values are saved in cells 513, 512 and 511, respectively. Note that cells 518, 558 and 514 are blank because the corresponding sensing vectors 18, 118 and 14 never detected a segment shift beyond the baseline segment threshold. From the foregoing information, further analysis would reveal that the non-physiologic event started proximate to the intersection region of the sensing vectors 116, 115, 16 and 12.

Returning to FIG. 3, at 318, it is determined whether a sufficient amount of ischemia progression data has been collected and entered in the vector table 500. For example, at 318, it may be determined whether a predetermined number of cardiac cycles have been measured. Alternatively, it may be determined at 318 whether the vector table has data values populated therein for predetermined time periods following the event start time for each sensing vector of interest. When more segment shift data is to be collected, flow returns along 320 and the operations of 312-316 are repeated. Alternatively, at 318, when a sufficient amount of ischemia progression data has been collected, flow moves to 322 where the data in the vector table is saved in long term memory in the IMD. Optionally, at 322, the vector table may be transmitted from the IMD to an external device, where the vector table is saved in memory or routed to a database, programmer, network computer and the like. At 322, other information associated with the non-physiologic event may also be saved with the vector table, such as morphology information, noncardiac indicators and the like. Once the vector table is saved at 320, the process is done at 324. Optionally, the vector tables may be cleared and repopulated periodically or each time a non-physiologic event is detected.

Figure 6:
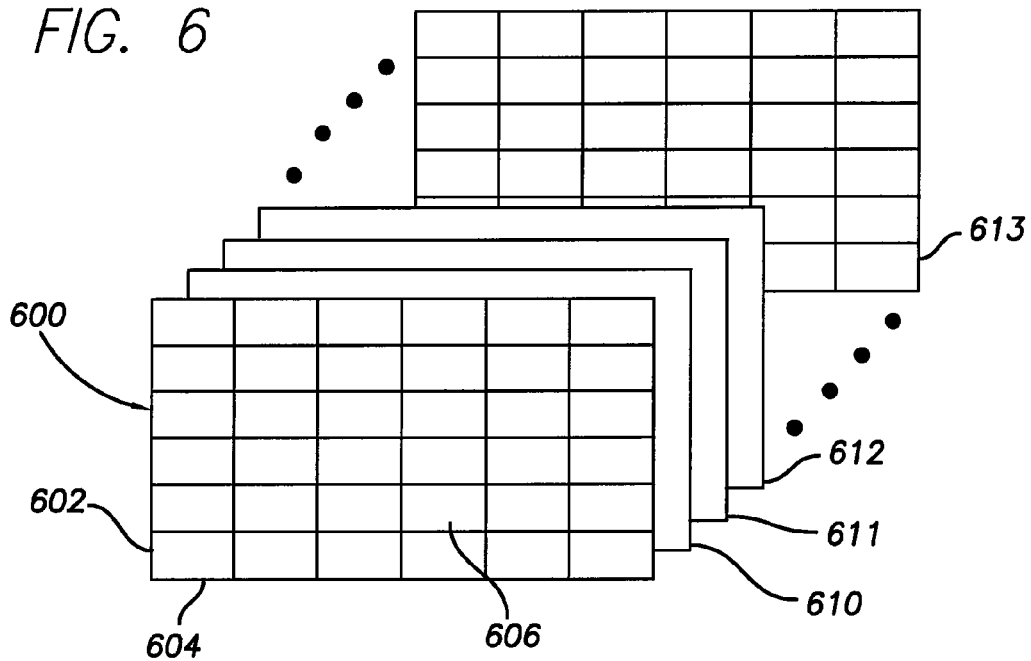
FIG. 6 illustrates a pictorial representation of a series of vector tables that may be collected over multiple non-physiologic events through the process of FIG. 3.

FIG. 6 illustrates a series 600 of vector tables 610-613 that may be collected in connection with detection of multiple non-physiologic events through the operations at 312-318 (FIG. 3). Each vector table 610-613 includes rows associated with a first group 602 of electrodes and columns associated with a second group of electrodes 604. Combinations of the electrodes in the first and second groups 602 and 604 define individual sensing vectors for which the corresponding cells 606 in the vector table are populated. A separate vector table may be created in connection with each non-physiologic event. Optionally, a common vector table may be created for multiple non-physiologic events.

Figure 7:
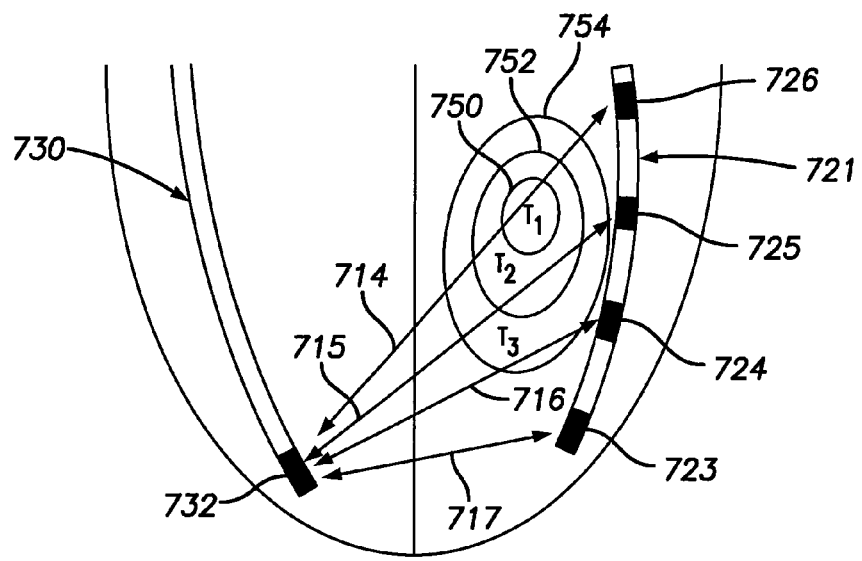
FIG. 7 illustrates an exemplary progression of an ischemic episode through a region of the heart at multiple time periods during the progression of the ischemic episode.
Figure 8:
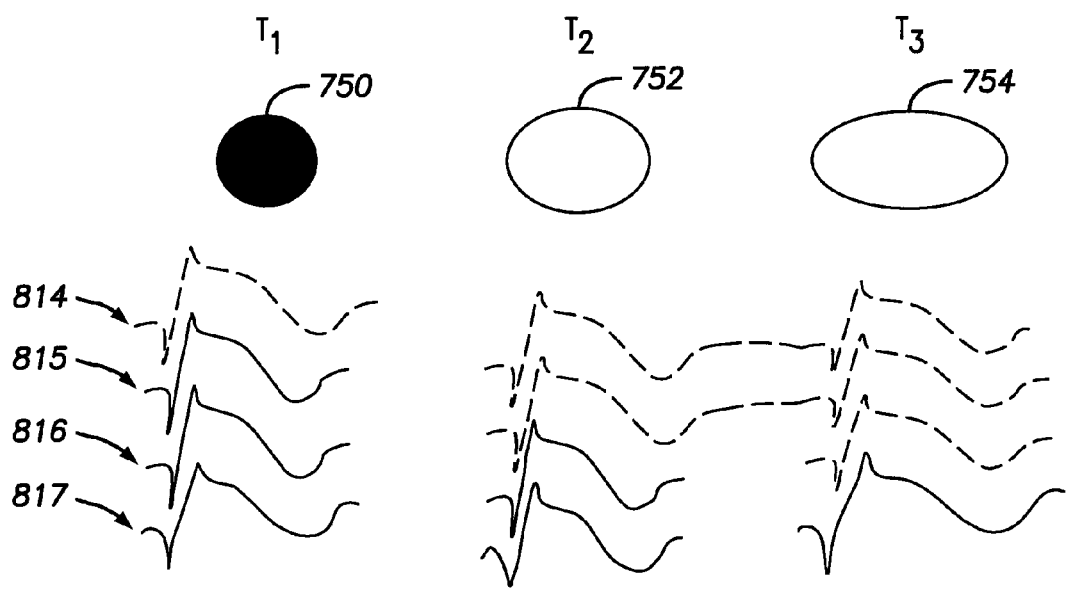
FIG. 8 illustrates exemplary cardiac signals that may be sensed over the sensing vectors of FIG. 7 at multiple time periods during the progression of the ischemic episode.

FIG. 7 illustrates a set or subset of exemplary sensing vectors and an ischemic region that is progressively growing over time following a non-physiologic event. FIG. 8 illustrates exemplary cardiac signals that may be collected from the sensing vectors of FIG. 7 at different times that correspond to different stages of progression by the ischemic event. Beginning with FIG. 7, a portion of an RV lead 730 is illustrated which includes an RV electrode 732 on the distal end thereof. A portion of an LV lead 721 is also illustrated including LV electrodes 723-726. Within the left ventricle, a region denoted at 750 corresponds to an initial region 750 that enters an ischemic state by time T1 which corresponds to the occurrence of a non-physiologic event. Optionally, time T1 may represent a short time period after the event start time (310 at FIG. 3). After the initial ischemic region 750 is formed, it grows to encompass the region 752 by time T2. A short period of time after time T2, the ischemic region continues to progress, thereby expanding to encompass the area denoted at 754 by time T3.

The electrodes 723-726 and 732 define sensing vectors 714-717. At successive sampling intervals, the region exhibiting an ischemic state grows and progressively crosses or approaches the sensing vectors 714-717. For example, at a time T1, only the sensing vector 714 directly crosses the tissue region 750 in an ischemic state. By time T2, the tissue region, that is intersected by sensing vectors 714, 715, has entered into an ischemic state. By time T3, the tissue region that intersects sensing vectors 714-716, has entered into the ischemic state.

Turning to FIG. 8, exemplary cardiac signals are illustrated in accordance with each of the sensing vectors 714-717 and for each of times T1-T3. The cardiac signals 814-817 are sensed along the sensing vectors 714-717, respectively in FIG. 7. Within FIG. 8, some of the cardiac signals are illustrated in solid line, while some are illustrated in shadow or dash lined to reflect that the cardiac signals in shadow line are either absent or have a segment shift that exceeds the baseline ST segment threshold. In FIG. 7, at time T1, when the region 750 enters an ischemic state, the cardiac signal 814 detected along sensing vector 714 is abnormal. The abnormal cardiac signal 814 exhibits an excessive segment shift which is detected at 314 in FIG. 3. At time T1, the sensing vectors 715-717 detect cardiac signals 815-817 that exhibit normal behavior (e.g., the segments of interest do not deviate beyond the baseline segment thresholds). Hence, at time T1, the process of FIG. 3 only adds ischemia progression data to the cell(s) of the vector table that correspond to the sensing vector 714, while the cells associated with sensing vectors 715-717 remain blank.

Next, at time T2, a new set of cardiac signals are collected at 312, and processed at 314 and ischemia progression data is recorded at 316. The region 752 now exhibits an ischemic state. Hence, the cardiac signals 814 and 815 associated with sensing vectors 714 and 715, exhibit abnormal behavior (e.g., exhibit segment shifts that deviate beyond the baseline segment threshold). At time T2, the cardiac signals 816 and 817 still exhibit normal physiologic behavior. Hence, at time T2, the process of FIG. 3 only adds ischemia progression data to the cell(s) of the vector table that correspond to the sensing vector 715, while the cell associated with sensing vectors 716-717 remain blank, and the cells associated with sensing vector 714 retains the ischemia progression data entered at time T1.

At time T3, when the region 754 exhibits an ischemic state, the cardiac signals 814-816 have abnormal characteristics (e.g., segment shifts beyond the baseline segment threshold). At time T3, the cardiac signal 817 still exhibits normal physiologic behavior or at least within acceptable limits of deviation in the segment shift. Hence, at time T3, the process of FIG. 3 only adds ischemia progression data to the cell(s) of the vector table that correspond to the sensing vector 716, while the cell(s) associated with sensing vector 717 remain blank, and the cells associated with sensing vectors 714 and 715 retain the progression data entered at times T1 and T2, respectively.

In accordance with the process of FIG. 3, the vector table is populated with timing information and/or segment shift information based on the cardiac signals 814-817 sensed during each of times T1-T3. The vector tables are uploaded from an IMD to a programmer, database, network and the like for subsequent analysis, such as in accordance with the process of FIG. 4. The vector tables may be presented graphically to physicians or analyzed and the results of such analysis presented to the physician. For example, visual graphics may be presented to indicate the progression of an ischemic area. The progression of the ischemic region may be shown in a simulated real time display. Thereafter, the data in the vector tables are processed in accordance with the operations of FIG. 4 to identify shift gradients for the sensing vectors, as well as vector angles and vector magnitudes associated with the gradient information. From the gradient information, the ischemic region and type of ischemia may be determined. For example, the size of the ischemic region, the direction of development within the ischemic region and the rate of the development of the ischemic region may be identified. From the size, direction and rate of progression information, it may then be determined whether the ischemic episode represents transient ischemia or a myocardial infarction.

While the foregoing examples are explained in connection with an LV lead having a quad-pole electrode configuration proximate the left ventricle, it is appreciated that other electrode configurations could be used. The sensing vectors in the path of an ischemic event will be relatively sensitive to the state of the ischemic region, thereby providing detailed timing information as well as the direction and rate of progression of the ischemic region. Optionally, one or more of the electrodes may represent a large surface area electrode, such as a coil which may yield more global information regarding a segment shift.

Figure 9:
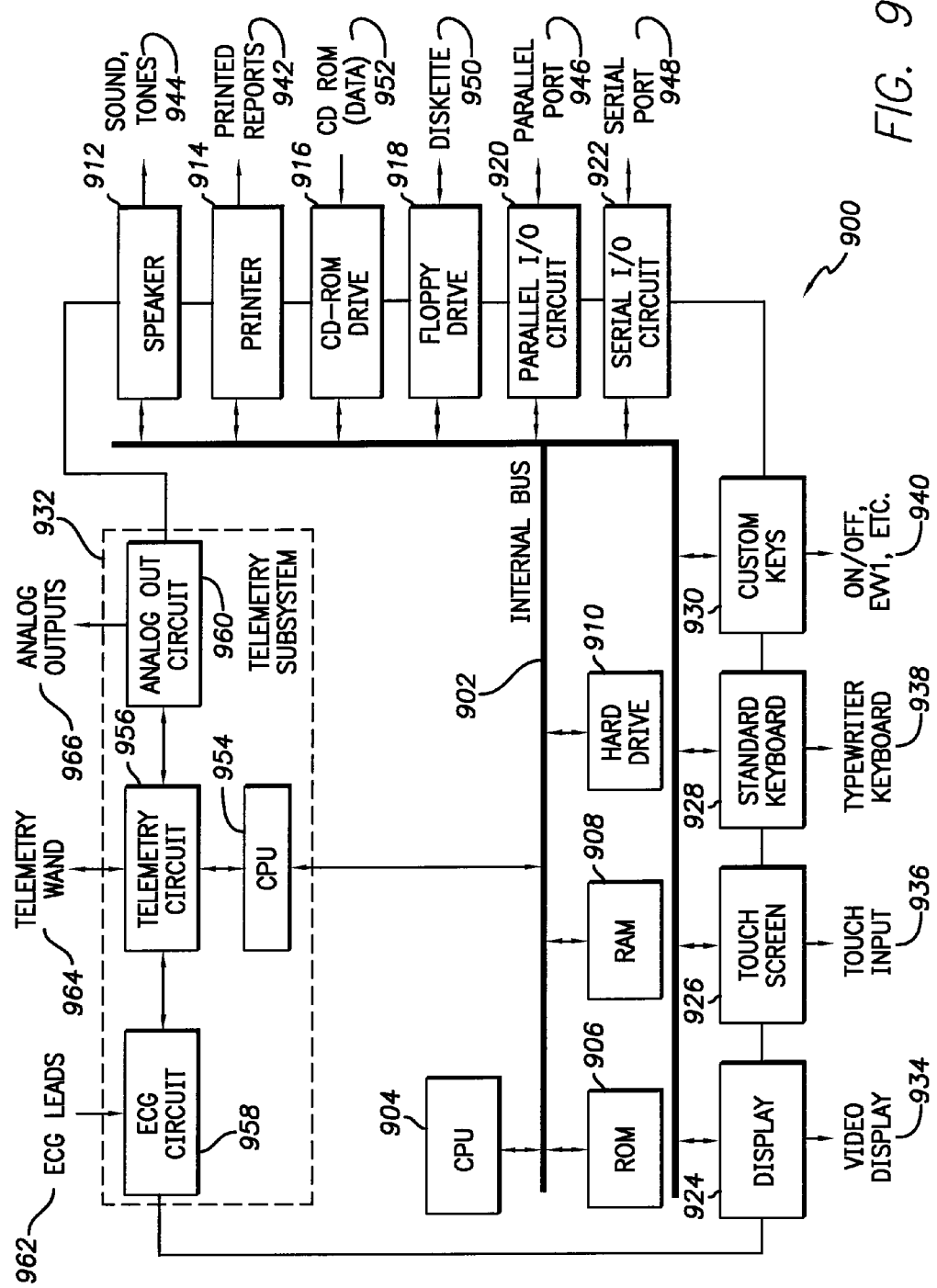
FIG. 9 illustrates a functional block diagram of an external device that may analyze the ischemia progression data in order to monitor ischemia and differentiate transient ischemia from persistent spreading ischemia.

FIG. 9 illustrates a functional block diagram of the external device 900, such as a programmer, that is operated by a physician, a health care worker, or a patient to interface with IMD 10 (shown in FIG. 1). The external device 900 may be utilized in a hospital setting, a physician's office, or even the patient's home to communicate with the IMD 10 to change a variety of operational parameters regarding the therapy provided by the IMD 10 as well as to select among physiological parameters to be monitored and recorded by the IMD 10. For example, the external device 900 may be used to program coronary episode related parameters, such as ischemia-related and AMI-related ST segment shift thresholds, duration thresholds, and the like. Further, the external device 900 may be utilized to interrogate the IMD 10 to determine the condition of a patient, to adjust the physiological parameters monitored or to adapt the therapy to a more efficacious one in a non-invasive manner.

External device 900 includes an internal bus 902 that connects/interfaces with a Central Processing Unit (CPU) 904, ROM 906, RAM 908, a hard drive 910, a speaker 912, a printer 914, a CD-ROM drive 916, a floppy drive 918, a parallel I/O circuit 420, a serial I/O circuit 922, the display 924, a touch screen 926, a standard keyboard connection 928, custom keys 930, and a telemetry subsystem 932. The internal bus 902 is an address/data bus that transfers information (e.g., either memory data or a memory address from which data will be either stored or retrieved) between the various components described. The hard drive 910 may store operational programs as well as data, such as reference ST segments, ST thresholds, impedance thresholds, other thresholds, timing information and the like.

The CPU 904 typically includes a microprocessor, a microcontroller, or equivalent control circuitry, designed specifically to control interfacing with the external device 900 and with the IMD 10 (shown in FIG. 1). The CPU 904 may further include RAM or ROM memory, logic and timing circuitry, state machine circuitry, and I/O circuitry to interface with the IMD 10. Typically, the microcontroller 222 (shown in FIG. 2) includes the ability to process or monitor input signals (e.g., data) as controlled by program code stored in memory (e.g., ROM 906).

The display 924 (e.g., may be connected to a video display 934) and the touch screen 926 display text, alphanumeric information, data and graphic information via a series of menu choices to be selected by the user relating to the IMD 10, such as for example, status information, operating parameters, therapy parameters, patient status, access settings, software programming version, ST segment thresholds, impedance thresholds, other thresholds, and the like. The touch screen 926 accepts a user's touch input 936 when selections are made. The keyboard 928 (e.g., a typewriter keyboard 938) allows the user to enter data to the displayed fields, operational parameters, therapy parameters, as well as interface with the telemetry subsystem 932. Furthermore, custom keys 930 turn on/off 940 (e.g., EVVI) the external device 900. The printer 914 prints hard-copies of reports 942 for a physician/healthcare worker to review or to be placed in a patient file, and speaker 912 provides an audible warning (e.g., sounds and tones 944) to the user in the event a patient has any abnormal physiological condition occur while the external device 900 is being used. The parallel I/O circuit 920 interfaces with a parallel port 446. The serial I/O circuit 922 interfaces with a serial port 948. The floppy drive 918 accepts diskettes 950. The CD-ROM drive 916 accepts CD ROMs 952.

The telemetry subsystem 932 includes a central processing unit (CPU) 954 in electrical communication with a telemetry circuit 956, which communicates with both an ECG circuit 958 and an analog out circuit 960. The ECG circuit 958 is connected to ECG leads 962. The telemetry circuit 956 is connected to a telemetry wand 964. The analog out circuit 932 includes communication circuits, such as a transmitting antenna, modulation and demodulation stages (not shown), as well as transmitting and receiving stages (not shown) to communicate with analog outputs 966. The external device 900 may wirelessly communicate with the IMD 10 and utilize protocols, such as Bluetooth, GSM, infrared wireless LANs, HIPERLAN, 3G, satellite, as well as circuit and packet data protocols, and the like. A wireless RF link utilizes a carrier signal that is selected to be safe for physiologic transmission through a human being and is below the frequencies associated with wireless radio frequency transmission. Alternatively, a hard-wired connection may be used to connect the external device 900 to IMD 10 (e.g., an electrical cable having a USB connection).

Figure 10:
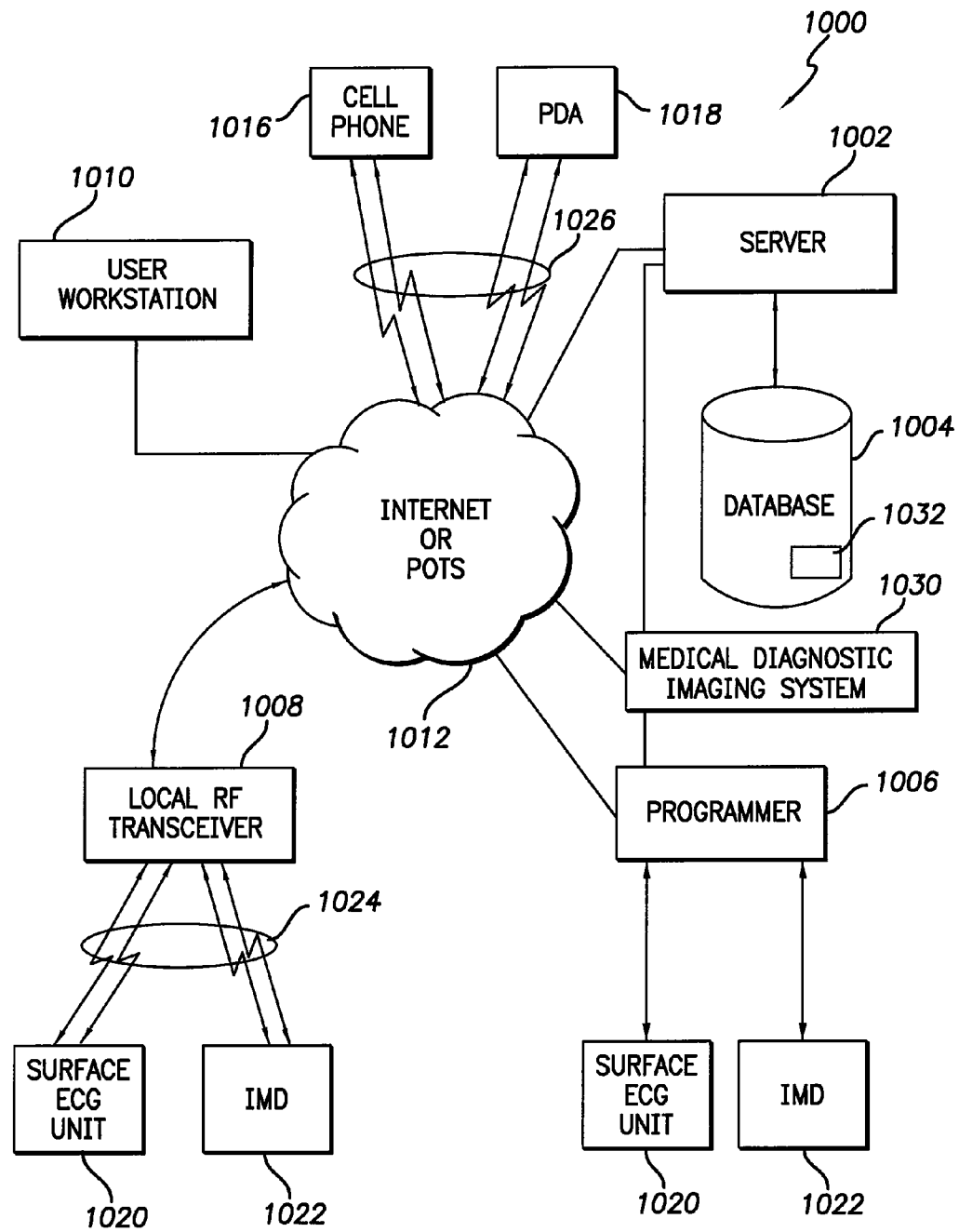
FIG. 10 illustrates a distributed processing system in accordance with one embodiment, whereby the progression data and vector tables are collected and routed for storage and analysis.

FIG. 10 illustrates a distributed processing system 1000 in accordance with one embodiment. The distributed processing system 1000 includes a server 1002 that is connected to a database 1004, a programmer 1006 (e.g., similar to external device 900 described above and shown in FIG. 9), a local RF transceiver 1008 and a user workstation 1010 electrically connected to a communication system 1012. The communication system 1012 may be the internet, a voice over IP (VoIP) gateway, a local plain old telephone service (POTS) such as a public switched telephone network (PSTN), and the like. Alternatively, the communication system 1012 may be a local area network (LAN), a campus area network (CAN), a metropolitan area network (MAN), or a wide area network (WAM). The communication system 1012 serves to provide a network that facilitates the transfer/receipt of cardiac signals, processed cardiac signals, histograms, trend analysis and patient status, and the like.

The server 1002 is a computer system that provides services to other computing systems (e.g., clients) over a computer network. The server 1502 acts to control the transmission and reception of information (e.g., cardiac signals, processed cardiac signals, ST segments, R-waves, thresholds, impedances, histograms, statistical analysis, trend lines, and the like). The server 1002 interfaces with the communication system 1012, such as the internet or a local POTS based telephone system, to transfer information between the programmer 1006, the local RF transceiver 1008, the user workstation 1010 as well as a cell phone 1016, and a personal data assistant (PDA) 1018 to the database 1004 for storage/retrieval of records of information. For instance, the server 1002 may download, via a wireless connection 1026, to the cell phone 1016 or the PDA 1018 the results of processed cardiac signals, ST segment trends, impedance vectors, or a patient's physiological state (e.g., is the patient having or has had an ischemia) based on previously recorded cardiac information. On the other hand, the server 1002 may upload raw cardiac signals (e.g., unprocessed cardiac data) from a surface ECG unit 1020 or an IMD 1022 via an RF link 1024 with the local RF transceiver 1008 or the programmer 1006.

Database 1004 is any commercially available database that stores information in a record format in electronic memory. The database 1004 stores information such as raw cardiac data, processed cardiac signals, statistical calculations (e.g., averages, modes, standard deviations), histograms, cardiac trends (e.g., STS trends), and the like. The information is downloaded into the database 1004 via the server 1002 or, alternatively, the information is uploaded to the server from the database 1004.

The programmer 1006 is similar to the external device 900 shown in FIG. 9 and described above, and may reside in a patient's home, a hospital, or a physician's office. Programmer 1006 interfaces with the surface ECG unit 1020 and the IMD 1022 (e.g., similar to the IMD 10 described above and shown in FIG. 1). The programmer 1006 may wirelessly communicate with the IMD 1022 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 1006 to IMD 10 (e.g., an electrical cable having a USB connection). The programmer 1006 is able to acquire cardiac signals from the surface of a person (e.g., ECGs), or the programmer is able to acquire intra-cardiac electrogram (e.g., IEGM) signals from the IMD 1022. The programmer 1006 interfaces with the communication system 1012, either via the internet or via POTS, to upload the cardiac data acquired from the surface ECG unit 1020 or the IMD 1022 to the server 1002. The programmer 1006 may upload more than just raw cardiac data. For instance, the programmer 1006 may upload status information, operating parameters, therapy parameters, patient status, access settings, software programming version, ST segment thresholds, calculated or measured impedance vectors, and the like.

The local RF transceiver 1008 interfaces with the communication system 1012, either via the internet or via POTS, to upload cardiac data acquired from the surface ECG unit 1020 or the IMD 1022 to the server 1002. In one embodiment, the surface ECG unit 1020 and the IMD 1022 have a bi-directional connection with the local RF transceiver via a wireless connection. The local RF transceiver 1008 is able to acquire cardiac signals from the surface of a person (e.g., ECGs), or acquire intra-cardiac electrogram (e.g., IEGM) signals from the IMD 1022. On the other hand, the local RF transceiver 1008 may download stored cardiac data from the database 1004 or the analysis of cardiac signals from the database 1004 (e.g., ST segment statistical analysis, ST segment trends, impedance vectors, and the like) information to the surface ECG unit 1020 or the IMD 1022.

The user workstation 1010 may interface with the communication system 1012 via the internet or POTS to download information via the server 1002 from the database 1004. Alternatively, the user workstation 1010 may download raw data from the surface ECG unit 1020 or IMD 1022 via either the programmer 1006 or the local RF transceiver 1008. Once the user workstation 1010 has downloaded the cardiac information (e.g., raw cardiac signals, ST segments, impedance vectors, and the like), the user workstation 1010 may process the cardiac signals, create histograms, calculate statistical parameters, or determine cardiac trends and determine if the patient is suffering from ischemia or another physiological condition. Once the user workstation 1010 has finished performing its calculations, the user workstation 1010 may either download the results to the cell phone 1016, the PDA 1018, the local RF transceiver 1008, the programmer 1006, or to the server 1002 to be stored on the database 1004.

FIG. 10 further illustrates a medical diagnostic imaging system (MDIS) 1030 that communicates with one or more of the internet 1012, server 1002 and programmer 1006. Optionally, the MDIS 1030 may communicate directly or indirectly with workstations 1010, cell phones 1016, PDAs 1018, the database 1004, surface ECG devices 1020, and/or IMDs 1022. The foregoing communications links to and from the MDIS 1030 may be wired or wireless. The medical diagnostic imaging system 1030 may be an magnetic resonance imaging (MRI) system, a computed tomography (CT) system, a positron emission tomography (PET) system, a nuclear medicine (NM) system, an ultrasound (UL) system, an electrophysiology (EP) system, a hemodynamic (HD) system, an intracardiac echocardiography (ICE) system and the like. The MDIS 1030 scans the patient to generate the corresponding type of imaging data (e.g., MRI, CT, PET, NM, UL, EP, HD, ICE data and the like). The imaging data may be stored in the database 1004 (as denoted at 1032), or elsewhere in the network, such as at the workstations 1010, cell phones 1016, PDAs 1018, and/or IMDs 1022.

The imaging data may represent raw imaging data corresponding to the modality by which the data was collected. For example, the imaging data may represent individual or sets of two-dimensional slices of data acquired by the corresponding modality. The imaging data may represent a three dimensional volume of acquired imaging data. Optionally, the imaging data may represent a series of 3D volumes that are acquired over time (e.g., 4D). Optionally, the imaging data may represent a series of 2D slices that are acquired over time (e.g., a cine loop). Optionally, the imaging data may be scan converted and/or rendered to form medical diagnostic images that are produced based on raw imaging data. The scan conversion and/or rendering operations may be performed at the MDIS 1030, server 1002, programmer 1006, workstations 1010, cell phones 1016, PDAs 1018 and the like, to produce medical diagnostic (MD) images. The MD images may then be stored in the database 1004 or elsewhere, such as at the MDIS 1030, server 1002, programmer 1006, workstations 1010, cell phones 1016, PDAs 1018 and the like.

Figure 4:
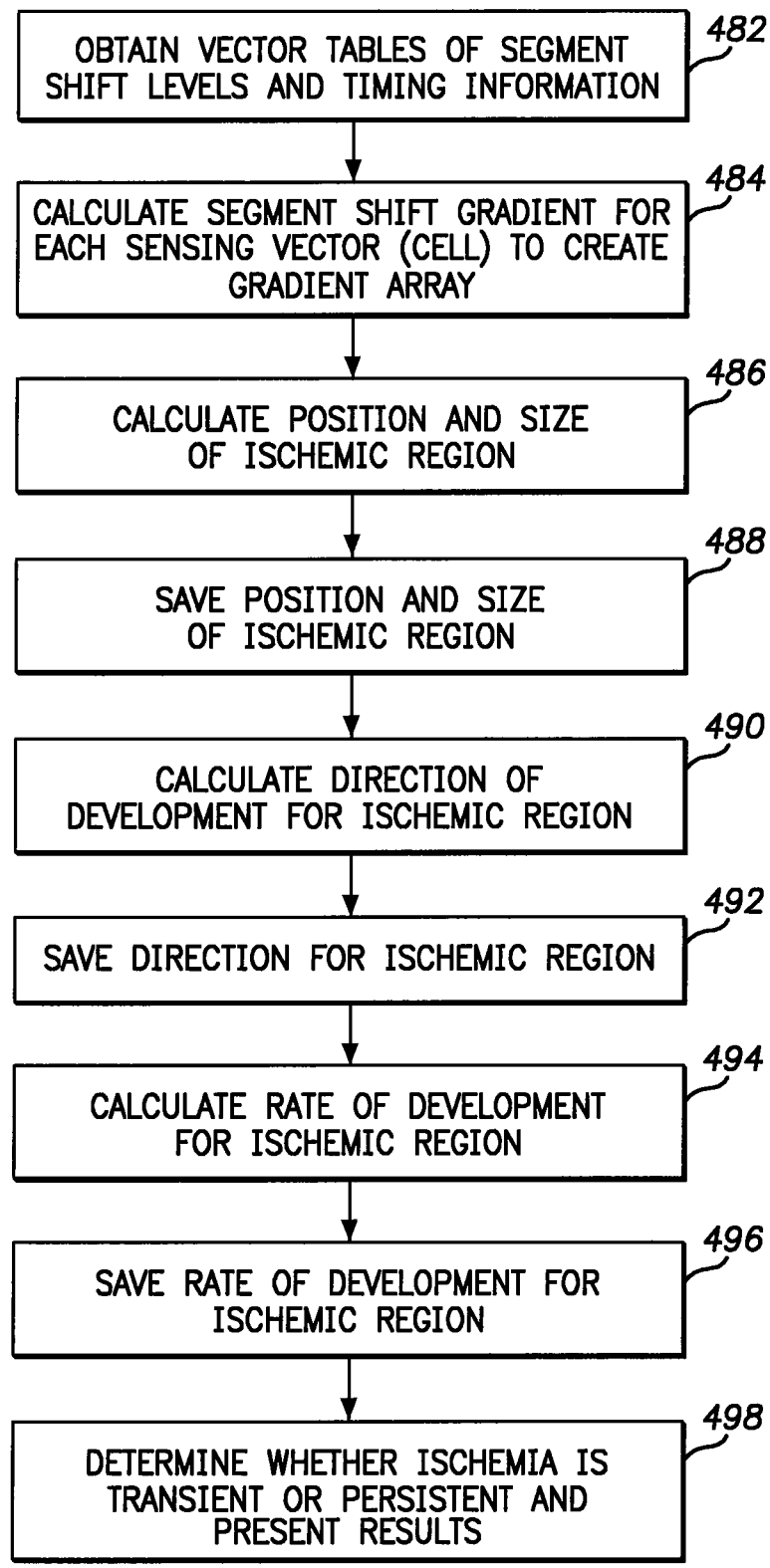
FIG. 4 illustrates a processing sequence carried out in accordance with an embodiment to analyze the ischemia progression data in order to monitor ischemia and differentiate transient ischemia from persistent spreading ischemia.

FIG. 4 illustrates a processing sequence carried out in connection with an embodiment to analyze the ischemia progression data in order to monitor ischemia and differentiate transient ischemia from persistent spreading ischemia. The process of FIG. 4 may be implemented by the IMD, an external home based device, a programmer, a physician's computer, a central analysis facility and the like. Beginning at 482, a vector table is obtained from memory, such as from the memory in an IMD, database, programmer, network server or the like. The vector table includes ischemia progression data such as shown in FIG. 5.

At 484, the process performs a gradient analysis upon the progression data in the vector table. For example, segment shift gradients may be calculated for each cell in the vector table. The segment shift gradients would then correspond to each sensing vector. For example, when the table in FIG. 5 includes timing differentials, the table creates a scalar field of timing differentials $\Delta T$ over the heart space. The timing differentials $\Delta T$ extend over the heart space defined by the sensing vectors, where each cell stores a local timing differential value $\Delta T(i,j)$, where i represents the table row and j represents the table column. For example, the process, at 484, may create a gradient field $G[\Delta T]$. The gradient field $G[\Delta T]$ includes an array of gradient vectors $G[\Delta T(i,j)]$, each of which corresponds to a cell (i,j) in the sensing vector space. Each of the gradient vectors $G[\Delta T(i,j)]$ includes an angle of propagation component and a magnitude component. The angle of propagation component identifies the direction in which the timing differential $\Delta T$ rises most quickly, while the magnitude component represents how fast the timing differential $\Delta T$ rises in the designated direction.

By way of example, the angle of propagation component may be calculated with the following formula: Magnitude=sqrt($(\Delta X^2+\Delta Y^2)$), where $\Delta X$ represents a sum of the relative changes in the timing differential $\Delta T$ in the x-direction from cell (i,j) and where $\Delta Y$ represents a sum of the relative changes in the timing differential $\Delta T$ in the y-direction from cell (i,j). The magnitude component may be calculated by the following formula: Angle=arc_cos((X dot Y)/abs (X) abs(Y) where X and Y is the vector originating from the reference cell (i,j).

Optionally, the gradient may also be used to measure how the scalar field $\Delta T$ changes in other directions, rather than just the direction of greatest change, by taking a dot product. If the timing differential function $\Delta T$ is differentiable, then the gradient of $\Delta T$ dotted with a unit vector gives the slope of the timing differential in the direction of the vector. More precisely, when $\Delta T$ is differentiable, the dot product of the gradient of $\Delta T$ with a given unit vector is equal to the directional derivative of $\Delta T$ in the direction of that unit vector. Once the gradient array is created at 404, flow moves to 406.

At 486, the process determines a position and size of the ischemic region. The position and size of the ischemic region may be calculated based on the vector table 500. Cells in the vector table that include timing differential values indicate that the corresponding regions of the tissue are in an ischemic state. The position and size of the ischemic region may be derived from how many cells in the vector table have timing differential values and/or from which cells in the vector table have timing differential values. For example, the sensing vectors may cover 50% of the heart tissue and two-thirds of the sensing vectors may detect excessive segment shifts. From this information, a size of the ischemic region may be estimated. Alternatively, the sensing vectors may each be attributed to a certain area or percentage of the heart tissue. For example, the sensing vectors 15-18 (FIG. 1A) may cover 25% of the heart tissue, while the sensing vectors 11-14 only cover 15%. Also, the position of the ischemic region may be calculated based on when sensing vectors detect the abnormal segment shift.

Optionally, the position and size of the ischemic region may be calculated based on the gradient field created at 484. The position and size of the ischemic region may be derived from how many gradient vectors in the array of the gradient field exceed a gradient threshold and by which gradient vectors in the array of the gradient field exceed a gradient threshold. For example, the sensing vectors may cover 50% of the heart tissue and one-fourth of the gradient vectors may exceed a gradient magnitude threshold. From this information, a size of the ischemic region may be estimated. Alternatively, the gradient vectors may each be attributed to a certain area or percentage of the heart tissue. For example, the sensing vectors 15-18 (FIG. 1A) may cover 25% of the heart tissue, while the sensing vectors 11-14 only cover 15%. Based on which gradient vectors exceed the threshold, the percentage of the heart tissue in an ischemic state would be calculated.

At 488, the position and size of the ischemic region is saved.

At 490, the process determines a progression direction in which the ischemic region is developing. The progression direction of the ischemic region may be calculated based on the gradient field. The gradient vectors in the array of the gradient field include direction and magnitude information.

The directions and magnitudes of the individual gradient vectors may be combined to determine an overall direction and magnitude in which the ischemic region is developing. At 492, the progression direction associated with the ischemic region is saved.

At 494, the process determines a progression rate at which the ischemic region is developing. The progression rate of the ischemic region may be calculated based on the gradient field. At 496, the progression rate for the ischemic region is saved.

At 498, it is determined whether the ischemic region is transient or persistent. The ischemic region is transient when the area of the region decreases over time. The ischemic region is persistent when the area of the region spreads and remains permanent over time. At 498, the process presents ischemia related information to a user on a graphical user interface (GUI), such as on a display of a computer or programmer, on through a printer and the like. When a severity of ischemia is related to the ΔST elevation/suppression, a 2-D GUI may be expanded by adding deviation of ΔST (e.g. by presenting different colors for different amplitude ranges of ST segment shift).

Figure 11:
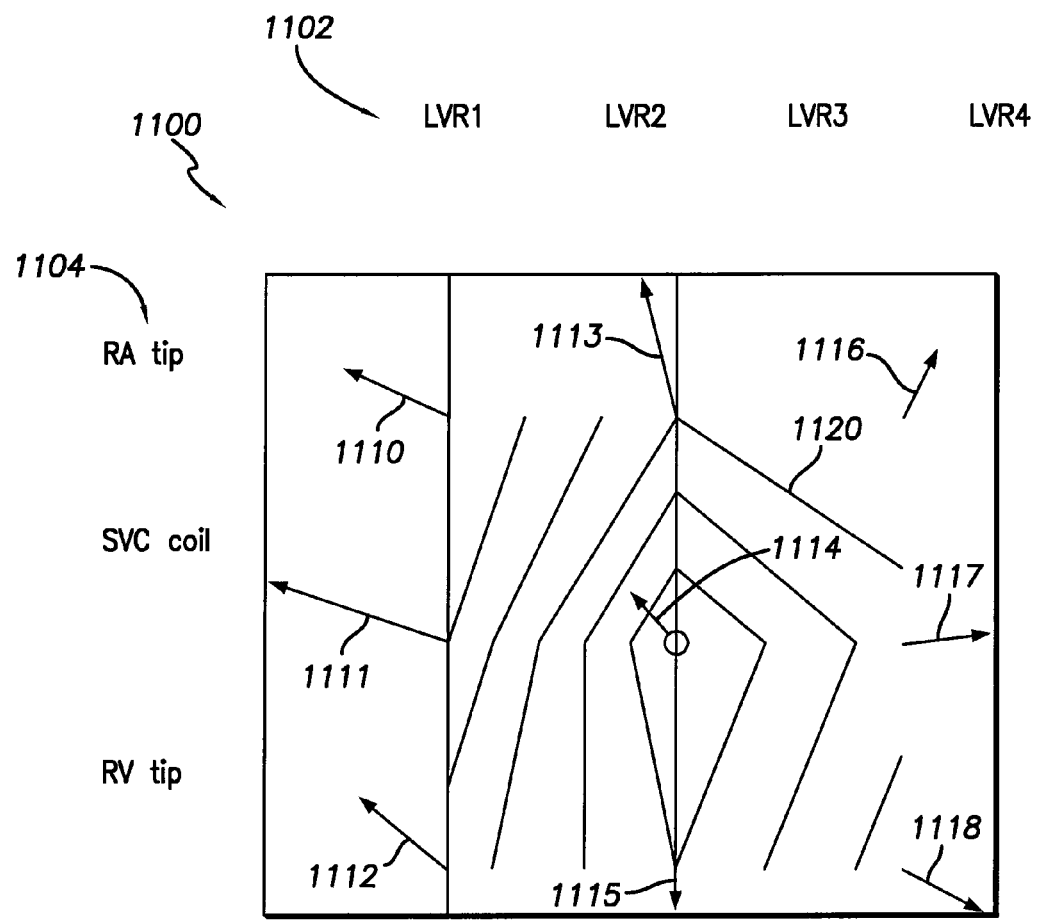
FIG. 11 illustrates an exemplary graph that may be presented to a user in accordance with an embodiment.

FIG. 11 illustrates an exemplary graph that may be presented to a user, such as on a display or printed. The graph 1100 represents a 2-D spatial area corresponding to the region of the heart from which cardiac signals are obtained. The horizontal axis includes the LV electrodes 1102 and the vertical axis includes the non-LV electrodes 1104. Gradient vectors 1110-1118 originate at the points of intersection between the LV and non-LV electrodes. The magnitude and direction of each gradient 1110-1118 is determined as discussed above based on the values of the progression data in the vector table. For example, the gradient vector 1114 corresponds to the region at which the ischemia started. The gradient vectors 1110-1112 point to the left (e.g., toward the RA or RV) which corresponds to a direction away from the ischemia starting point, while the gradient vectors 1116-1118 point to the right (e.g., toward the apex of the LV).

The graph 1100 also includes lines of progression 1120 which illustrate the general directions of development of the ischemic region. The lines of progression 1120 may be coded, such as through color coding or the like, to indicate a rate at which the ischemic region develops in the corresponding direction. The lines of progression 1120 are developed based on the angle and magnitude of the gradient vectors 1110-1118.

Figure 12:
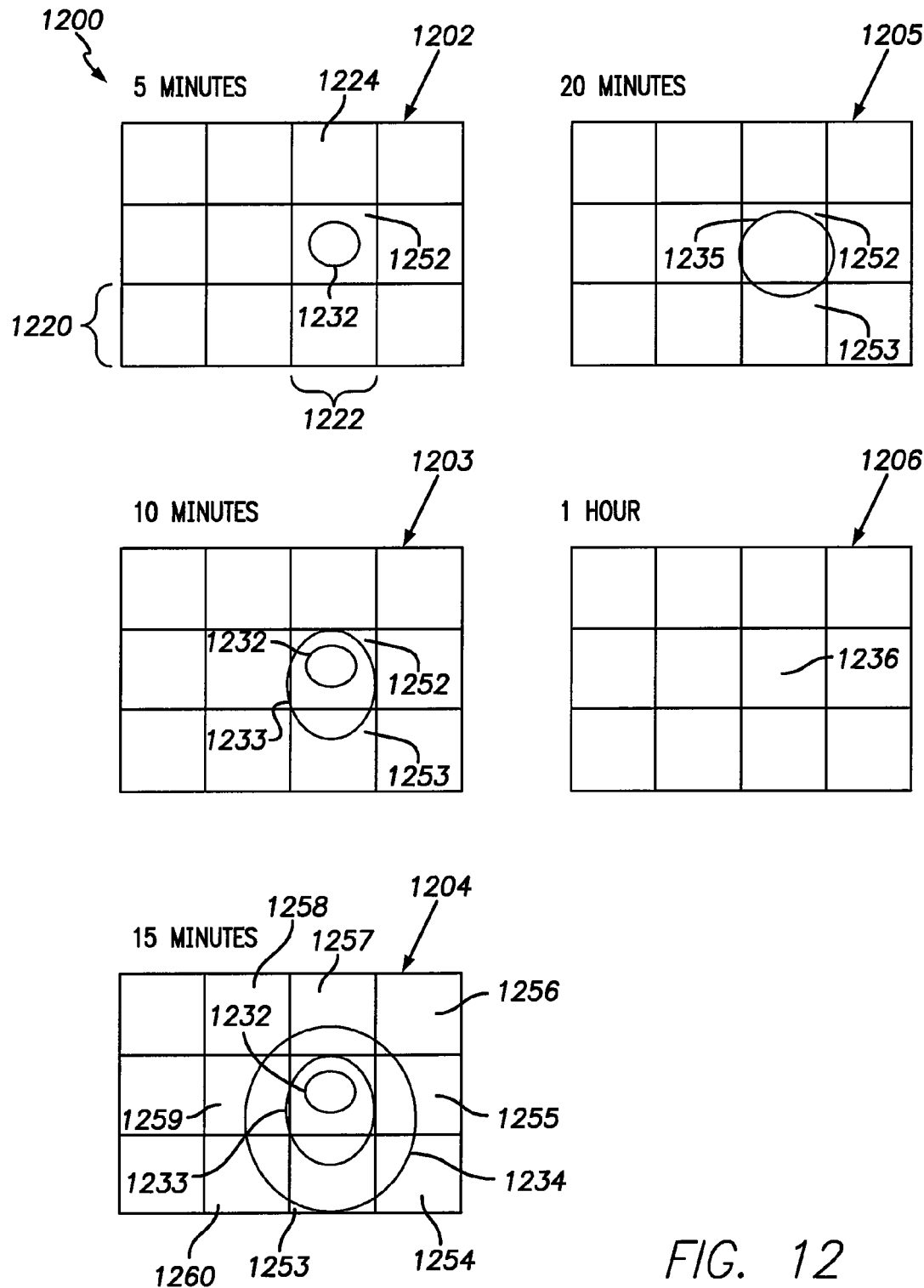
FIG. 12 illustrates an exemplary presentation in which ischemia progression information is provided to a user related to transient ischemia.

FIG. 12 illustrates an exemplary presentation in which ischemia progression information is provided to a user related to transient ischemia. The presentation 1200 includes a series of "bulls-eye" ischemic state plots 1202-1206. The plots 1202-1206 are temporally distributed over a collection time period in which multiple cardiac cycles are sensed and analyzed. Each of the plots 1202-1206 correspond to a different time slot within the collection time period relative to a point in time at which a non-physiologic event was detected. The plots 1202-1206 present a grid layout of cells 1224 defined by rows 1220 and columns 1222. The rows 1220 and columns 1222 correspond to non-LV electrodes and LV electrodes, respectively. The cells 1224 correspond to the regions of the heart associated with the sensing vectors defined by the non-LV and LV electrodes.

In the example of FIG. 12, a non-physiologic event occurred at time zero. State plots 1202-1206 are presented to the user at predetermined time intervals following the non-physiologic event, such as 5 minutes, 10 minutes, 15 minutes, 20 minutes, and one hour after the non-physiologic event. The state plot 1202 illustrates a location and size of the ischemic region 1232 five minutes after the occurrence of the non-physiologic event. The ischemic region 1232 covers a portion of the cell 1252 which corresponds to the region of the heart associated with the SVC coil electrode 38 and the LV electrode 25 (FIG. 1A). Within 5 minutes following the non-physiologic event, the region 1232 is relatively small in comparison to the overall heart size.

The state plot 1203 illustrates a location and size of the ischemic region 1233 ten minutes after the occurrence of the non-physiologic event. The ischemic region 1233 covers all of the cell 1252 and has expanded into the cell 1253 which collectively correspond to the regions of the heart associated with the SVC coil electrode 38 and the LV electrode 25 and the RV tip electrode 32 and the LV electrode 25. Within 10 minutes following the non-physiologic event, the region 1233 has grown to roughly double in size. Optionally, the original region 1232 may be illustrated in the state plot 1203 overlaid within the region 1233.

The state plot 1204 illustrates a location and size of the ischemic region 1234 fifteen minutes after the occurrence of the non-physiologic event. The ischemic region 1234 covers all of cell 1252 and has expanded into the cells 1253-1260. The cells 1252-1260 correspond to the regions of the heart associated with the non-LV electrodes (RA tip, SVC coil and RV coil) and the LV electrodes 23-25 shown in FIG. 5. Within 15 minutes following the non-physiologic event, the region 1233 has grown by roughly five times in size. Optionally, the original region 1232 and intermediate region 1233 may be illustrated in the state plot 1204 overlaid within the region 1235.

The state plot 1205 illustrates a location and size of the ischemic region 1234 twenty minutes after the occurrence of the non-physiologic event. The ischemic region 1235 has reduced in size from the size in plot 1204. The ischemic region 1235 covers only a portion cell 1252 and a portion of cell 1253. Optionally, the original region 1232 and intermediate regions 1233 and 1235 may be shown in shadow line or removed entirely.

The state plot 1206 illustrates a location and size of the ischemic region 1236 one hour after the occurrence of the non-physiologic event. The ischemic region 1236 has reduced in size from the size in the prior plot 1202-1205. The ischemic region 1236 covers only a small portion of cell 1252.

By illustrating the progression of the size and position of the ischemic region over time, a user can determine through visual inspection whether an ischemia is transient or persistent. Optionally, the automated processes described herein can be used to analyze the ischemia progression information and automatically classify transient and persistent ischemia.

FIG. 11 illustrates a block diagram of exemplary manners in which embodiments of the present invention may be stored, distributed and installed on a computer-readable medium. In FIG. 11, the "application" represents one or more of the methods and process operations discussed above. For example, the application may represent the process carried out in connection with FIGS. 1 through 9 as discussed above.

Figure 13:
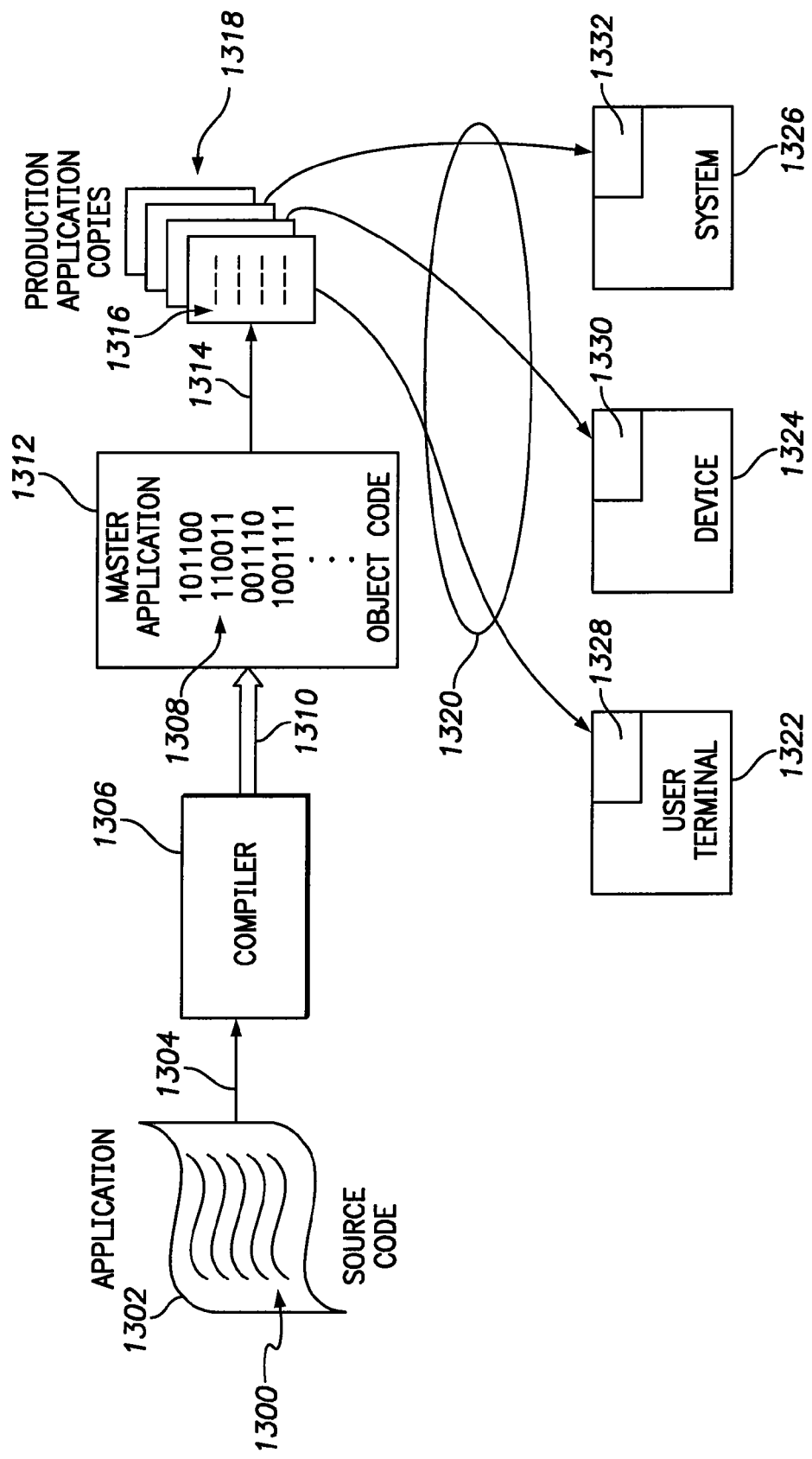
FIG. 13 illustrates a block diagram of exemplary manners in which embodiments may be stored, distributed and installed on a computer-readable medium.

As shown in FIG. 13, the application is initially generated and stored as source code 1300 on a source computer-readable medium 1302. The source code 1300 is then conveyed over path 1304 and processed by a compiler 1306 to produce object code 1308. The object code 1308 is conveyed over path 1310 and saved as one or more application masters on a master computer-readable medium 1312. The object code 1308 is then copied numerous times, as denoted by path 1314, to produce production application copies 1316 that are saved on separate production computer-readable medium 1318. The production computer-readable medium 1318 is then conveyed, as denoted by path 1320, to various systems, devices, terminals and the like. In the example of FIG. 13, a user terminal 1322, a device 1324 and a system 1326 are shown as examples of hardware components, on which the production computer-readable medium 1318 are installed as applications (as denoted by 1328 through 1332). For example, the production computer-readable medium 1318 may be installed on the IMD 10 (shown in FIG. 1) and/or the controller 900 (shown in FIG. 9).

The source code may be written as scripts, or in any high-level or low-level language. Examples of the source, master, and production computer-readable medium 1302, 1312 and 1318 include, but are not limited to, CDROM, RAM, ROM, Flash memory, RAID drives, memory on a computer system and the like. Examples of the paths 1304, 1310, 1314, and 1320 include, but are not limited to, network paths, the internet, Bluetooth, GSM, infrared wireless LANs, HIPERLAN, 3G, satellite, and the like. The paths 1304, 1310, 1314, and 1320 may also represent public or private carrier services that transport one or more physical copies of the source, master, or production computer-readable medium 1302, 1312 or 1318 between two geographic locations. The paths 1304, 1310, 1314 and 1320 may represent threads carried out by one or more processors in parallel. For example, one computer may hold the source code 1300, compiler 1306 and object code 1308. Multiple computers may operate in parallel to produce the production application copies 1316. The paths 1304, 1310, 1314, and 1320 may be intra-state, inter-state, intra-country, inter-country, intra-continental, inter-continental and the like.

The operation noted in FIG. 13 may be performed in a widely distributed manner world-wide with only a portion thereof being performed in the United States. For example, the application source code 1300 may be written in the United States and saved on a source computer-readable medium 1302 in the United States, but transported to another country (corresponding to path 1304) before compiling, copying and installation. Alternatively, the application source code 1300 may be written in or outside of the United States, compiled at a compiler 1306 located in the United States and saved on a master computer-readable medium 1312 in the United States, but the object code 1308 transported to another country (corresponding to path 1314) before copying and installation. Alternatively, the application source code 1300 and object code 1308 may be produced in or outside of the United States, but production application copies 1316 produced in or conveyed to the United States (for example, as part of a staging operation) before the production application copies 1316 are installed on user terminals 1322, devices 1324, and/or systems 1326 located in or outside the United States as applications 1328 through 1332.

Figure 14:
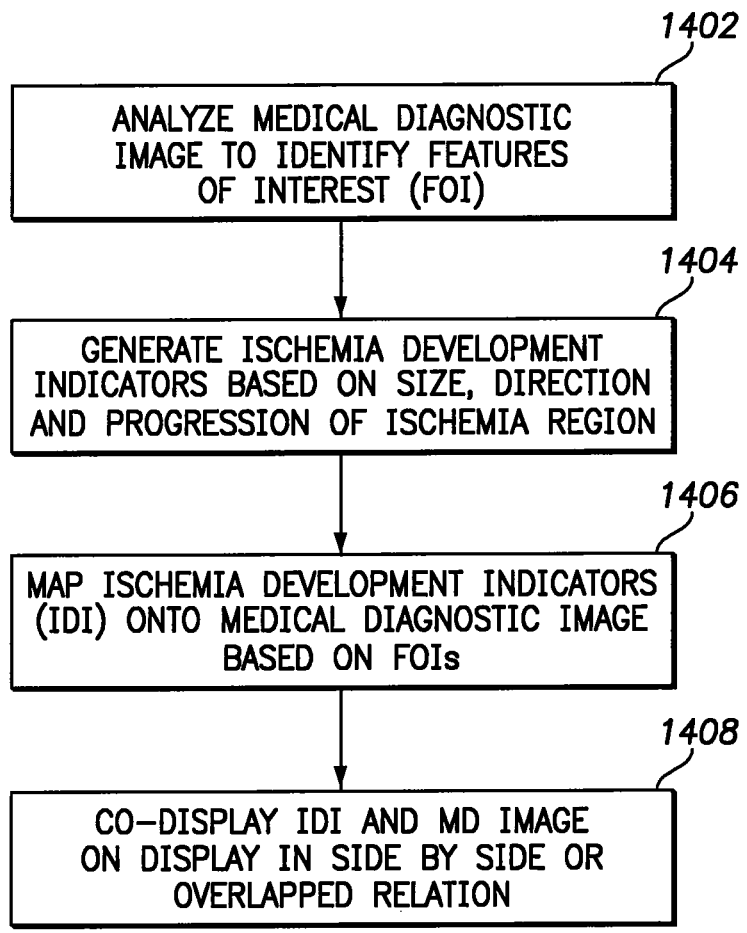
FIG. 14 illustrates a method implemented in accordance with an embodiment for presenting ischemia development information to the physician.

As used throughout the specification and claims, the phrases "computer-readable medium" and "instructions configured to" shall refer to any one or all of (i) the source computer-readable medium 1302 and source code 1300, (ii) the master computer-readable medium and object code 1308, (iii) the production computer-readable medium 1318 and production application copies 1316 and/or (iv) the applications 1328 through 1332 saved in memory in the terminal 1322, device 1324 and system 1326. FIG. 14 illustrates a method implemented in accordance with an embodiment for presenting ischemia development information to the physician. At 1402, the method obtains one or more medical diagnostic (MD) images from the database 1004, the MDIS 1030, server 1002, programmer 1006, workstations 1010, cell phones 1016, PDAs 1018 and the like. The MD images may be created prior to, or during the operations of FIG. 14 based on the imaging data obtained by the MDIS 1030 (FIG. 10). The MD images may represent 2D or 3D images. For example, a MD image may represent a volume rendered or surface rendered 3D image of the heart or of a portion of the heart from a desired view angle.

At 1402, the MD image(s) is analyzed to identify one or more features of interest (FOI) in the MD image. For example, the FOI may be one or more points or line segments on an implantable lead that form landmarks. Alternatively, the FOI may be an anatomical landmark such as the apex of the right ventricle, the wall between the left and right ventricles, the atrial-ventricular (AV) node, the mitral valve and the like.

At 1404, the method generates one or more ischemia development indicators (IDI) based on the size of an ischemia region, a direction of development of the ischemia region and/or a rate of progression of the ischemia region (which is obtained in accordance with the above discussed methods and systems). For example, the IDI may represent a bulls eye chart, regions that is shaded (e.g., in color or black-and-white), a border line and the like. The IDI may represent a colored or shaded line to identify the size of the ischemia region. Optionally, the IDI may represent a shaded area that is colored to identify the direction of development of the ischemia region and/or a rate of progression of the ischemia region. Optionally, one or more arrows may be utilized as part of, or alone, the IDI to indicate the direction of development of an ischemia region. Optionally, the IDI may include coding to indicate the rate of progression of the ischemia region. Optionally, each IDI may be sized and shaped to overlay and follow the sensing vector or vectors to which the IDI corresponds.

Optionally, the content of the IDI may be obtained from a look-up table (LUT) stored in memory. The content of the IDI may include colors, IBM shading, shape and/or arrow size that is cross referenced to ranges or values of ST segment shifts. Different content of the IDI may be accessed from the LUT based upon the amount of deviation in the ST segment shift for a particular region from the baseline ST segment shift.

At 1406, the IDI is mapped onto the MD image(s) based on the FOIs. For example, the FOIs may represent an RV electrode and one or more LV electrodes. The IDI may be a rectangular strip overlay that is positioned to overlap and extend between the RV electrode and corresponding LV electrodes. The overlay of the IDI may be colored based on a significance of the deviation in the segment of interest (e.g., an amount of deviation in the ST segment).

At 1408, the IDI and MD image are co-displayed in an overlapping manner with the IDI superimposed over the MD image.

Figure 15:
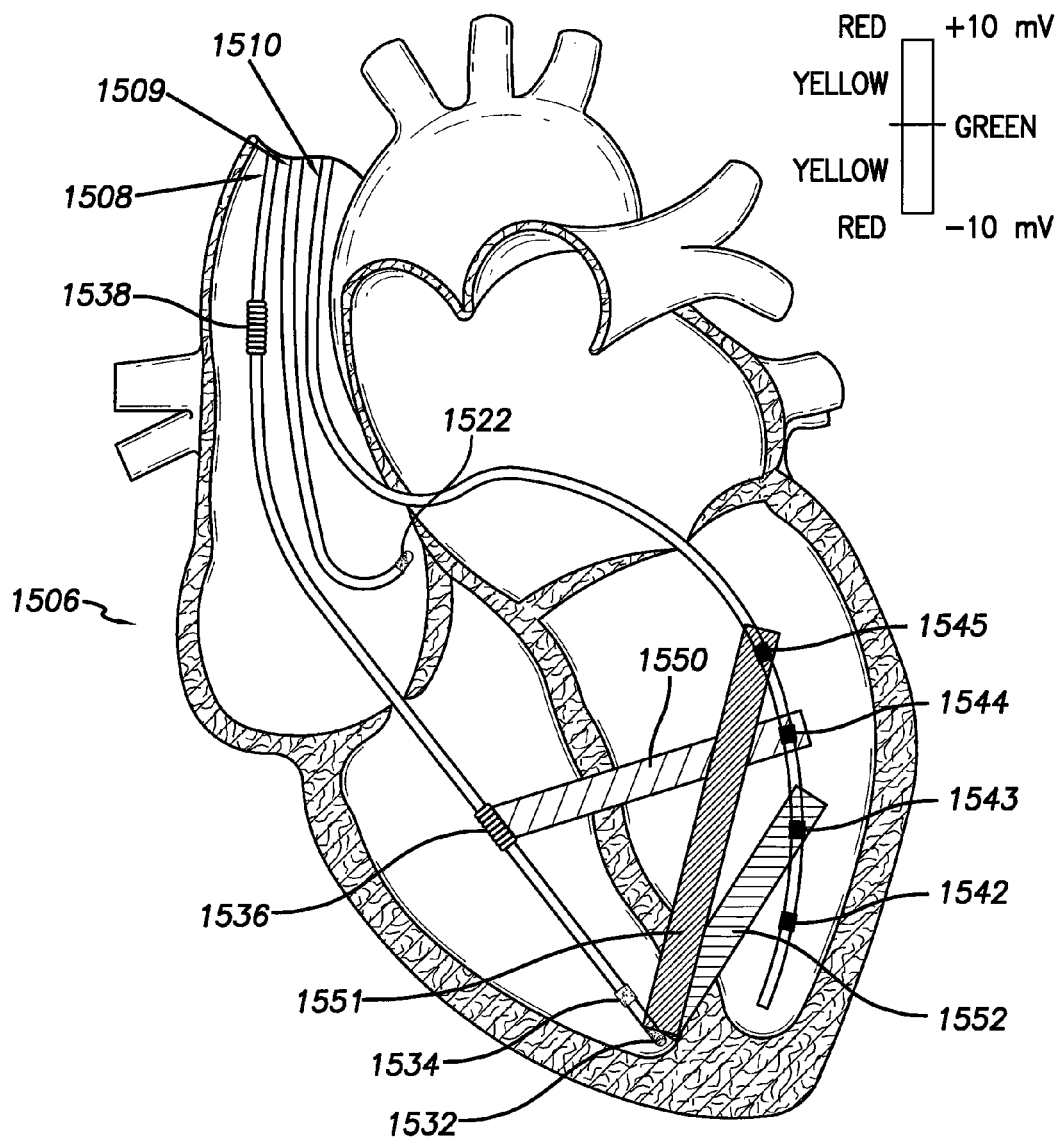
FIG. 15 illustrates an example of the IDI and MD image co-displayed and superimposed over one another in accordance with an embodiment.

FIG. 15 illustrates an example of the IDI and MD image co-displayed and superimposed over one another in accordance with an embodiment. FIG. 15 illustrates a volume rendered MD image 1506 of the heart. The MD image 1506 may be gray scale or colored. Optionally, the MD image 1506 may present anatomical structure (e.g., heart tissue and heart walls) in gray scale and functional information (e.g., blood flow) in color. Optionally, the MD image may be a 2D cross section of the heart taken along the sagittal axis, coronal axis or any other arbitrary cut plane through the heart. Optionally, the MD image may include multiple 2D and/or 3D images of the heart that are co-displayed side-by-side and presented from different view angles.

The MD image 1506 also illustrates distal portions of leads 1508-1510. The leads 1508-1510 may be part of the imaging data collected by the MIDS. Optionally, the leads 1508-1510 may be graphical representations of leads that are created separate from the imaging data and then superimposed on the MD image 1506.

The lead 1508 includes RV electrodes 1532, 1534 and 1536 located at the tip, distal region and intermediate region, respectively, of the RV chamber. The lead 1508 also includes a RA electrode 1538 located proximate the SVC. The lead 1509 includes RA electrode 1522 located in the distal region of the RA chamber. The lead 1510 includes LV electrodes 1542-1545 arranged along the lateral wall of the LV chamber.

FIG. 15 includes IDI regions 1550-1552 that are configured as rectangular strips and overlaid on the MD image 1506. Optionally, the IDI regions may not be rectangular strips, but instead the IDI regions may be square, oval, circular, triangular or any other shape. The IDI regions are partially transparent such that the structural and functional information in the MD image 1506 is visible through the IDI regions. The IDI regions 1550-1552 are positioned and oriented such that opposite ends of the IDI regions 1550-1552 are located at corresponding electrodes along an associated sensing vector. For example, the IDI region 1550 extends between RV electrode 1536 and LV electrode 1544. The IDI region 1550 is colored based on an amount of the ST segment sensed by the sensing vector that extends between RV electrode 1536 and LV electrode 1544. For example, if the ST segment shift detected between RV electrode 1536 and LV electrode 1544 is +5 mV, the IDI region 1550 is colored yellow. The IDI region 1551 extends between RV electrode 1532 and LV electrode 1545. The IDI region 1551 is colored based on an amount of the ST segment sensed by the sensing vector that extends between RV electrode 1532 and LV electrode 1545. For example, if the ST segment shift detected between RV electrode 1532 and LV electrode 1545 is -10 mV, the IDI region 1550 is colored red. The IDI region 1552 extends between RV electrode 1532 and LV electrode 1543. The IDI region 1552 is colored based on an amount of the ST segment sensed by the sensing vector that extends between RV electrode 1532 and LV electrode 1543. For example, if the ST segment shift detected between RV electrode 1532 and LV electrode 1543 is 0 mV, the IDI region 1550 is colored green.

Figure 16:
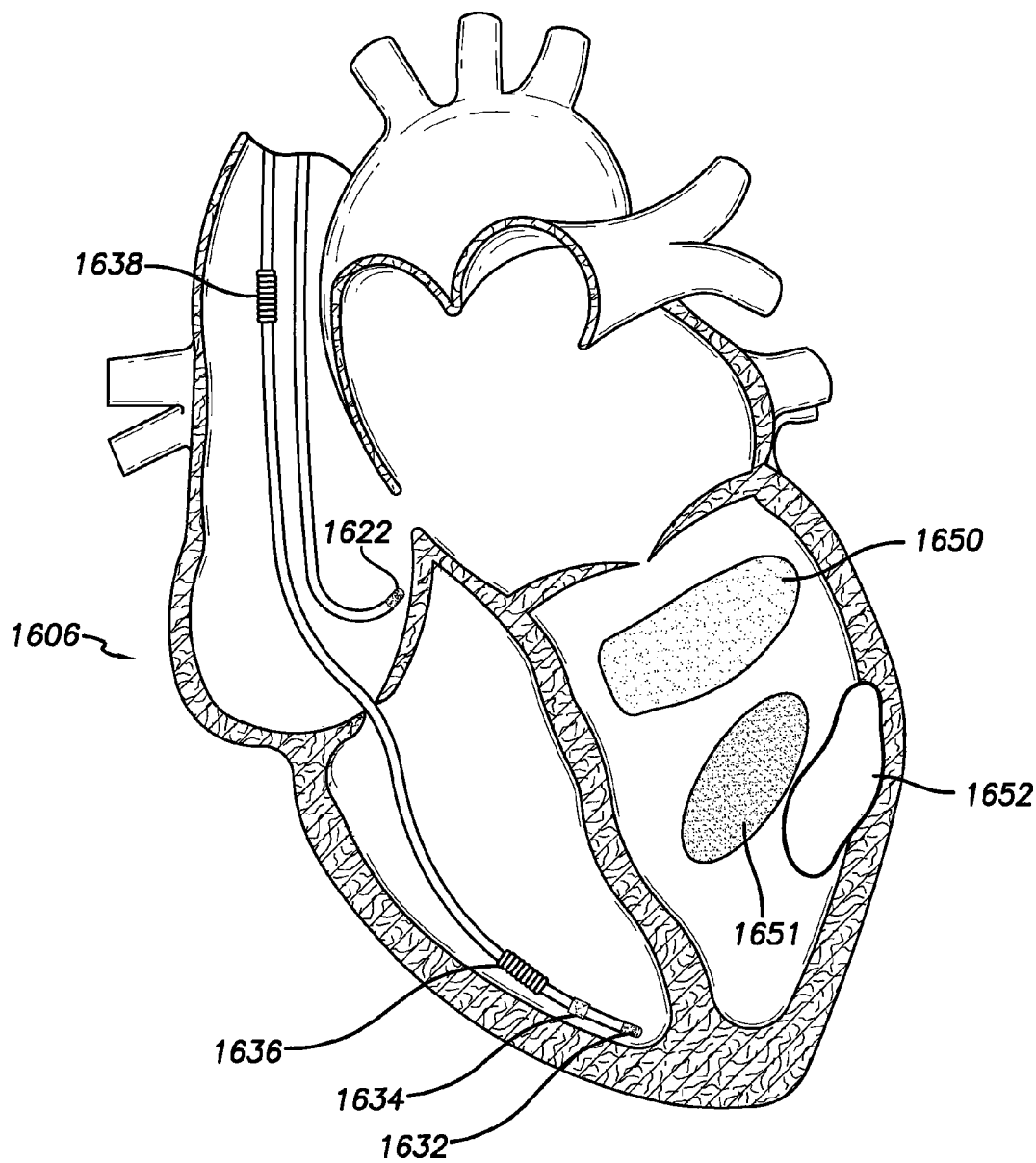
FIG. 16 illustrates another example of the IDI and MD image co-displayed and superimposed over one another in accordance with an embodiment.

FIG. 16 illustrates another example of the IDI and MD image co-displayed and superimposed over one another in accordance with an embodiment. FIG. 16 illustrates a 2D cross sectional MD image 1606 of the heart. The MD image 1606 also illustrates distal portions of leads 1608 and 1609 (lead 1610 may is not illustrated as it may not be located in the slice that corresponds to the MD image 1606. The lead 1608 includes RV electrodes 1632, 1634 and 1636 located at the tip, distal region and intermediate region, respectively, of the RV chamber. The lead 1608 also includes a RA electrode 1638 located proximate the SVC. The lead 1609 includes RA electrode 1622 located in the distal region of the RA chamber.

FIG. 16 includes IDI regions 1650-1652 that are overlaid on the MD image 1606. The ischemia regions 1650-1652 do not align with specific sensing vectors. Instead, the ischemia regions 1650-1652 represent regions of the heart that have been identified to exhibit transient or persistent ischemia. For example, region 1650 may indicate a region of the heart that exhibit transient ischemia and thus is colored or shaded in a color or shade that represents transient ischemia (or a degree of transient ischemia). Region 1651 may be colored or shaded to represent persistent ischemia. The IDI regions may not be shaded regions, but instead may simply represent a border that traces about an ischemia region and/or traces around an area that includes a corresponding sensing vector. For example, region 1652 may be outlined with an IDI border that is colored or shaded in a manner associated with the corresponding type or amount of ischemia (e.g., the rate of progression or the severity of the ST segment shift deviation). Optionally, a MD image may be displayed side by side with the IDI information in separate images.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A method for monitoring ischemic development, comprising:
    implanting at least one implantable lead having at least one LV electrode Proximate to a left ventricle;
    identifying an abnormal sinus rhythm using the at least one implantable lead;
    obtaining cardiac signals along multiple sensing vectors, wherein at least a portion of the sensing vectors extend to or from the at least one LV electrode located proximate to the left ventricle;
    monitoring a segment of interest in the cardiac signals that occurred after the detection of the abnormal sinus rhythm, the cardiac signals being obtained along the multiple sensing vectors using a processor adapted to identify deviations in the segment of interest from a baseline;
    recording at least one of timing or segment shift information associated with the deviations in the segments of interest; and
    identifying at least one of size, direction of development or rate of progression of an ischemia region based on the at least one of timing or segment shift information.

2. The method of claim 1, wherein the identifying operation identifies the rate of progression and provides graphical information regarding ischemic progression.

3. The method of claim 1, wherein the identifying operation includes differentiating transient ischemia from persistent spreading ischemia.

4. The method of claim 1, further comprising providing a first electrode proximate at least one of a right ventricle, right atrium and superior vena cava; providing multiple LV electrodes proximate to the left ventricle, wherein the sensing vectors extend between the first electrode and the multiple LV electrodes.

5. The method of claim 1, wherein the monitoring operation monitors the segment of interest as collected along multiple sensing vectors that extend through different portions of the LV.

6. The method of claim 1, wherein the deviations identified represent shifts in ST segments away from a baseline ST segment level.

7. The method of claim 1, wherein the recording operation includes populating a vector table with time and shift information associated with the deviations by the segment of interest.

8. The method of claim 1, further comprising calculating 2 dimension (2D) gradients in connection with the sensing vectors, the 2D gradient representing a change in the segment shift information per unit of time.

9. The method of claim 1, wherein the identifying operation identifies the size of the ischemia at successive points in time.

10. The method of claim 1, further comprising classifying an event as transient ischemia when the size of the ischemic region decreases over time.

11. The method of claim 1, further comprising co-displaying a medical diagnostic image of the heart with ischemia development information representative of at least one of the size, direction of development or rate of progression of an ischemia region.

12. A system for monitoring ischemic development, comprising:
at least one implantable lead having electrodes to obtain cardiac signals along multiple sensing vectors, wherein at least a portion of the sensing vectors extend to or from electrodes adapted for implantation proximate to a left ventricle;
an implantable device to identify an abnormal sinus rhythm;
a monitor module to monitor a segment of interest in the cardiac signals obtained along the multiple sensing vectors and that occurred after the abnormal sinus rhythm, the ischemia monitor module to identify deviations in the segment of interest from a baseline;
memory to record at least one of timing or segment shift information associated with the deviations in the segments of interest; and
an analysis module to identify at least one of size, direction of development or rate of progression for an ischemia region based on the at least one of timing or segment shift information.

13. The system of claim 12, wherein the analysis module identifies the rate of progression and provides graphical information regarding ischemic progression.

14. The system of claim 12, wherein the analysis module differentiates transient ischemia from persistent spreading ischemia.

15. The system of claim 12, wherein the at least one lead includes a first lead having a first electrode proximate to at least one of a right ventricle, right atrium and superior vena cava and a second lead having multiple LV electrodes proximate to the left ventricle, wherein the sensing vectors extend between the first electrode and the multiple LV electrodes.

16. The system of claim 12, wherein the monitoring module monitors the segment of interest as collected along multiple sensing vectors that extend through different regions of the LV.

17. The system of claim 12, wherein the monitoring module identifies deviations that represent shifts in ST segments away from a baseline ST segment level.

18. The system of claim 12, wherein the memory includes a vector table populated with the at least one of time and shift information associated with the deviations by the segment of interest.

19. The system of claim 12, wherein the analysis module calculates 2 dimension (2D) gradients in connection with the sensing vectors, the 2D gradient representing a change in the segment shift information per unit of time.

20. The system of claim 12, wherein the analysis module identifies the size of the ischemia at successive points in time.

21. The system of claim 12, wherein the analysis module classifies an event as transient ischemia when a size of the ischemic region decreases over time.

22. The system of claim 12, wherein the analysis module classifies an event as a persistent spreading ischemia when the ischemic region spreads by a predetermined amount and persists for a predetermined period of time.

23. The system of claim 12, further comprising a display to co-display a medical diagnostic image of the heart with ischemia development information representative of at least one of the size, direction of development or rate of progression of an ischemia region.

* * * * *